US009801614B2

(12) United States Patent
Takagi et al.

(10) Patent No.: US 9,801,614 B2
(45) Date of Patent: Oct. 31, 2017

(54) ULTRASOUND DIAGNOSTIC APPARATUS, ULTRASOUND IMAGE PROCESSING METHOD, AND NON-TRANSITORY COMPUTER READABLE RECORDING MEDIUM

(71) Applicant: Konica Minolta, Inc., Tokyo (JP)

(72) Inventors: Kazuya Takagi, Toyonaka (JP); Yuki Matsumoto, Settsu (JP); Tomohito Sakai, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 51 days.

(21) Appl. No.: 14/463,063

(22) Filed: Aug. 19, 2014

(65) Prior Publication Data

US 2015/0057544 A1 Feb. 26, 2015

(30) Foreign Application Priority Data

Aug. 21, 2013 (JP) .................................. 2013-171036
Aug. 13, 2014 (JP) .................................. 2014-164845

(51) Int. Cl.
*A61B 8/00* (2006.01)
*A61B 8/08* (2006.01)
*G06T 7/00* (2017.01)

(52) U.S. Cl.
CPC ............ *A61B 8/463* (2013.01); *A61B 8/0875* (2013.01); *A61B 8/4209* (2013.01);
(Continued)

(58) Field of Classification Search
CPC ... A61B 8/0875; A61B 8/4209; A61B 8/4405; A61B 8/486; A61B 8/488
See application file for complete search history.

(56) References Cited

U.S. PATENT DOCUMENTS

2006/0239523 A1* 10/2006 Stewart ................... G06T 19/20
382/128
2008/0187544 A1* 8/2008 Burkly ................. A61K 38/177
424/158.1
(Continued)

FOREIGN PATENT DOCUMENTS

CN 102973293 A 3/2013
JP 2013-056156 A 3/2013

OTHER PUBLICATIONS

Koike T.; The new concept of rheumatoid arthritis care—ultrasonography for joints; Medical Review Co., Ltd.; Mar. 2010; pp. 40-43.
(Continued)

*Primary Examiner* — Baisakhi Roy
(74) *Attorney, Agent, or Firm* — Lucas & Mercanti, LLP

(57) ABSTRACT

An ultrasound diagnostic apparatus includes an ultrasound image acquirer, an evaluation target determiner, a disease progression score calculator, a selector, and a display controller. The ultrasound image acquirer acquires ultrasound image signals of a plurality of frames. The evaluation target determiner analyzes the ultrasound image signal of each frame and determines the frame to be an evaluation target frame when the ultrasound image signal includes a target image section depicting a joint. The disease progression score calculator calculates, for each evaluation target frame, a disease progression score quantifying disease activity using an ultrasound image signal of the target image section included in the ultrasound image signal of the evaluation target frame. The selector selects at least one disease progression score in accordance with a predetermined numerical process. The display controller controls the display to display the selected disease progression score and an ultrasound image of a corresponding frame.

18 Claims, 33 Drawing Sheets

(52) U.S. Cl.
CPC .......... *A61B 8/5223* (2013.01); *G06T 7/0012* (2013.01); *A61B 8/4405* (2013.01); *A61B 8/486* (2013.01); *A61B 8/488* (2013.01); *A61B 8/5276* (2013.01); *G06T 2207/10132* (2013.01); *G06T 2207/10136* (2013.01)

(56) References Cited

U.S. PATENT DOCUMENTS

| | | | | |
|---|---|---|---|---|
| 2008/0194640 | A1* | 8/2008 | Nakamura | C07D 231/12 514/341 |
| 2009/0270272 | A1* | 10/2009 | Karl | G01N 33/564 506/9 |
| 2010/0256504 | A1* | 10/2010 | Moreau-Gaudry | A61B 5/0066 600/476 |
| 2011/0263948 | A1* | 10/2011 | Verbruggen | A61B 6/505 600/300 |
| 2013/0060121 | A1* | 3/2013 | Patwardhan | G06K 9/3241 600/407 |
| 2014/0017235 | A1* | 1/2014 | Rosenthal | A61K 39/3955 424/133.1 |
| 2014/0066469 | A1* | 3/2014 | Robinson | A61K 31/4706 514/275 |

OTHER PUBLICATIONS

Office Action dated Sep. 5, 2016 from corresponding Chinese Application; Application No. 201410415059.7; Applicant: Konica Minolta, Inc.; English translation of Office Action; Total of 20 pages.

Office Action dated Jun. 1, 2017 from the corresponding Chinese Application No. CN 201410415059.7 and English translation.

\* cited by examiner

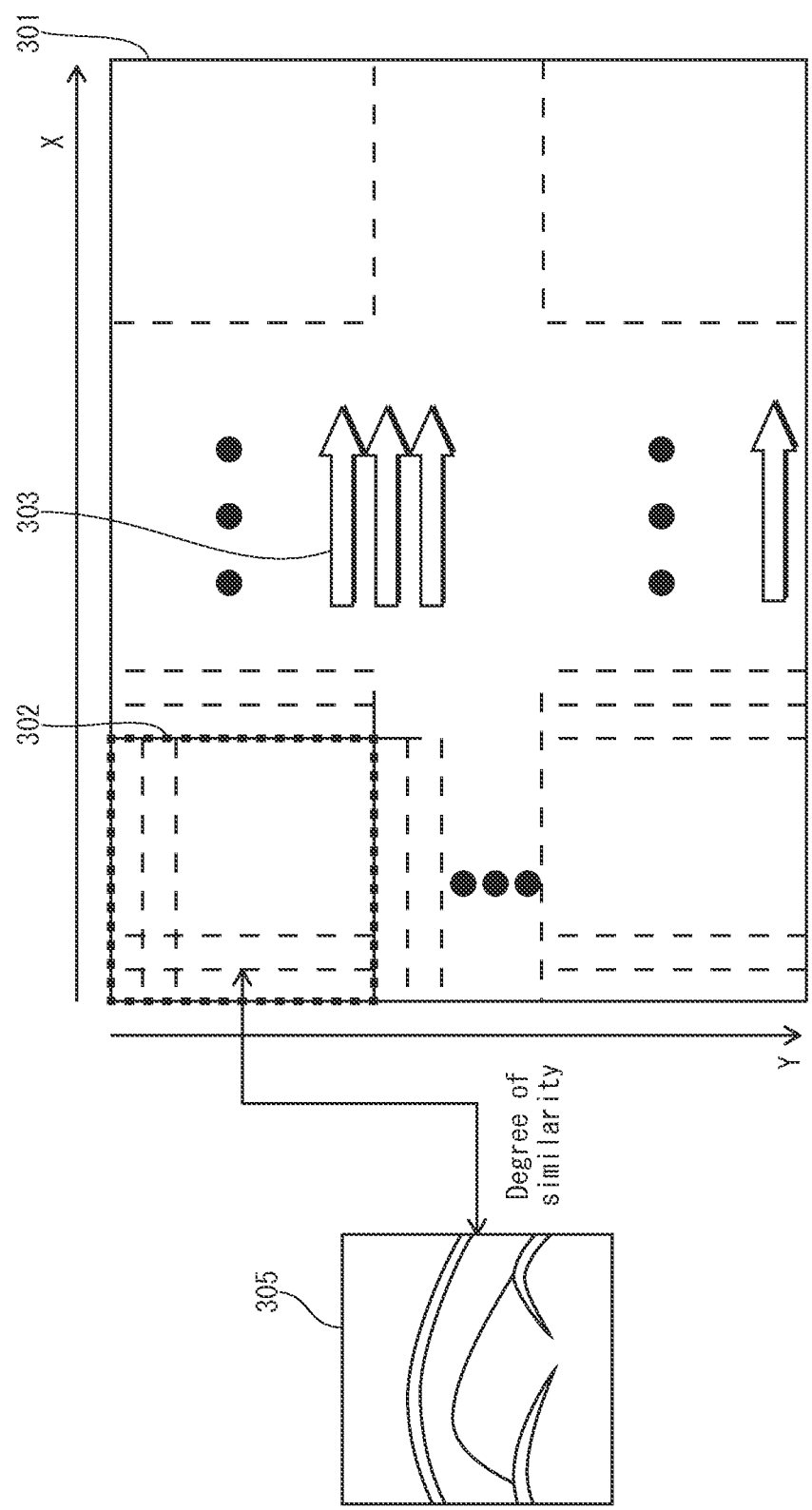

ULTRASOUND DIAGNOSTIC APPARATUS, ULTRASOUND IMAGE PROCESSING METHOD, AND NON-TRANSITORY COMPUTER READABLE RECORDING MEDIUM

CROSS REFERENCE TO RELATED APPLICATION

This Application claims the priority of Japanese Patent Application No. 2013-171036 filed on Aug. 21, 2013 and Japanese Patent Application No. 2014-164845 filed on Aug. 13, 2014, both applications are incorporated by reference herein.

BACKGROUND OF THE INVENTION (1) Field of the Invention

The present disclosure belongs to the technical field of ultrasound image processing methods. In particular, the present disclosure relates to an ultrasound image processing method that quantifies a degree of rheumatoid arthritis, and to an ultrasound diagnostic apparatus that uses the aforementioned method.

(2) Description of the Related Art

Ultrasound diagnostic apparatuses have conventionally been used to examine body parts such as the heart or abdomen, or to examine a fetus. In recent years, as a consequence of improved ultrasound diagnostic apparatus analytical ability, it has also become possible to use an ultrasound diagnostic apparatus to examine body parts close to the surface of the body. Therefore, an ultrasound diagnostic apparatus may be used in the field of orthopedics in order to examine body parts such as bones, tendons, and muscles, or may be used to evaluate inflammation of a joint in diagnosis of rheumatoid arthritis.

Evaluation of rheumatic inflammation is performed using a B-mode image and a Doppler mode image (for example, Takao KOIKE; The New Concept of Rheumatoid Arthritis Care -Ultrasonography for Joints-; Medikaru-Rebyu-Sha; p 40-43; Mar. 10, 2014). More specifically, the B-mode image is used to examine thickness of an articular cavity, presence of bone erosion, and build-up of synovial fluid, whereas the Doppler mode image is used to examine presence of angiogenesis.

In clinical research there is much interest in methods for quantifying a degree of inflammation. For example, previously proposed methods include a semi-quantitative method of subjectively categorizing inflammation into four stages, a BOX method of counting Doppler signals in a rectangular area, and a trace method of counting Doppler signals in a triangular area of which bones form two sides. Disease quantification such as described above is useful in determining the effectiveness of treatment.

SUMMARY OF THE INVENTION

Problems to be Solved by the Invention

However, evaluation results differ depending on which cross-section of a subject is evaluated by acquiring an ultrasound image thereof. Therefore, a problem exists that evaluation results are dependent on procedural skill and subjective judgments of an examiner.

In order to solve the above problem, an objective of the present disclosure is to provide an ultrasound diagnostic apparatus, an ultrasound image processing method, and a non-transitory computer readable recording medium, that reduce a degree to which an evaluation result is dependent on an examiner

Means for Solving the Problems

In order to achieve the above objective, one aspect of the present disclosure relates to an ultrasound diagnostic apparatus for selecting an ultrasound image signal of at least one frame from among ultrasound image signals of a plurality of frames acquired with respect to a subject through an ultrasound probe, and displaying the ultrasound image signal of the frame that is selected on a display, the ultrasound diagnostic apparatus comprising a control circuit including: an ultrasound image acquirer that acquires the ultrasound image signals of the plurality of frames; an evaluation target determiner that analyzes the ultrasound image signal of each of the frames and that determines the frame to be an evaluation target frame when the ultrasound image signal of the frame includes a target image section depicting a joint; a disease progression score calculator that calculates, for each evaluation target frame that is determined, a disease progression score quantifying activity of a disease, the disease progression score calculator calculating the disease progression score using an ultrasound image signal of the target image section included in the ultrasound image signal of the evaluation target frame; a selector that selects, in accordance with a predetermined numerical process, at least one disease progression score from among disease progression scores that are calculated; and a display controller that controls the display to display the disease progression score that is selected and an ultrasound image of a frame for which the disease progression score that is selected is calculated.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 10 relates to operation during the process for joint searching in the ultrasound diagnostic apparatus 1100;

DESCRIPTION OF THE PREFERRED EMBODIMENT

<<Embodiment>>
<Configuration>

The following explains, with reference to the drawings, an ultrasound diagnostic apparatus 1100, an ultrasound image processing method, and an ultrasound diagnostic system 1000 including the ultrasound diagnostic apparatus 1100, as relating to one embodiment of the present invention.

1. Overall Configuration of Ultrasound Diagnostic System 1000

Figure 1:
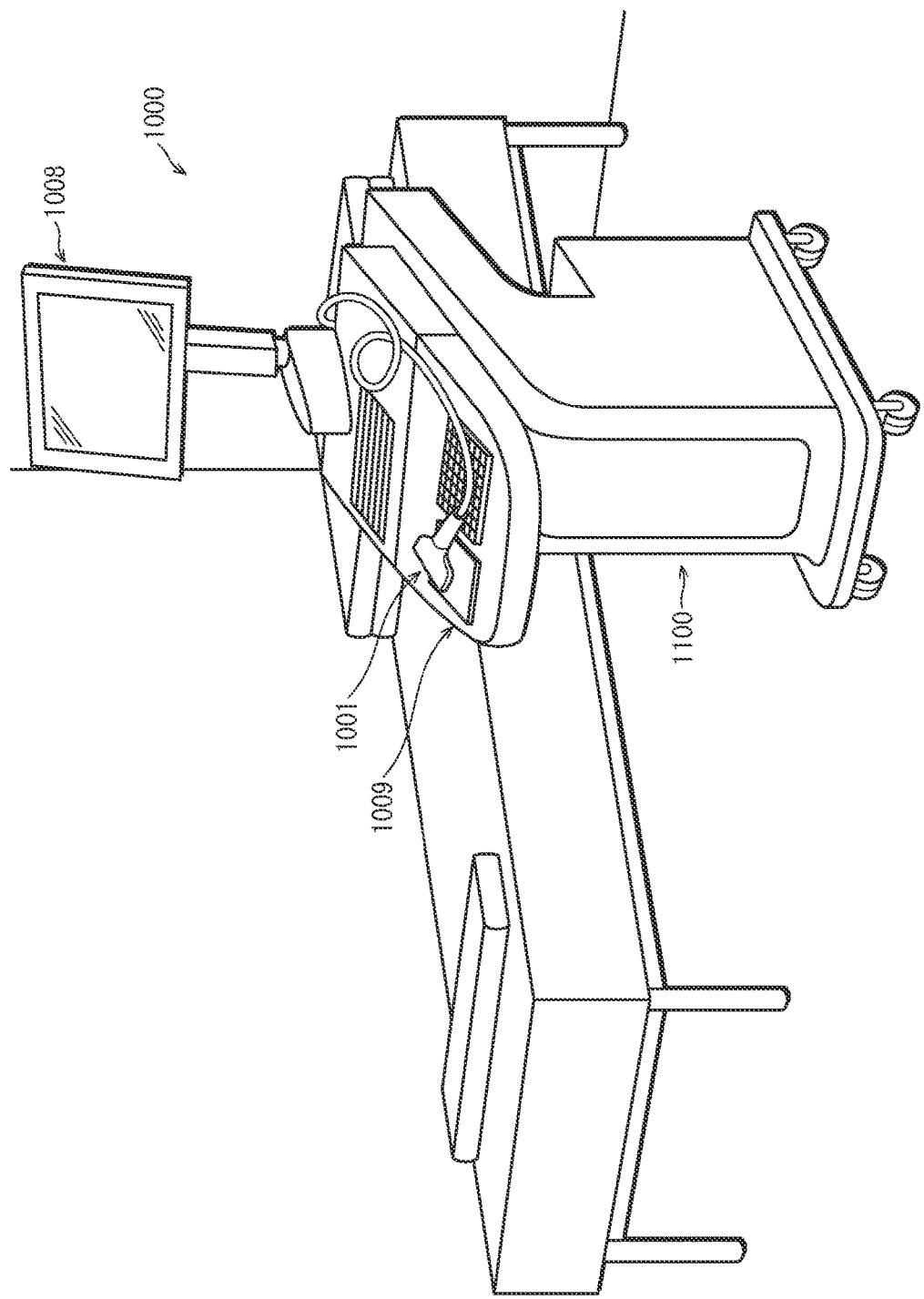
FIG. 1 illustrates an external view of an ultrasound diagnostic system 1000 including an ultrasound diagnostic apparatus 1100.

The following explains general configuration of the ultrasound diagnostic apparatus 1100 relating to the present embodiment. FIG. 1 illustrates an external view of the ultrasound diagnostic system 1000 in which the ultrasound diagnostic apparatus 1100 is included. In addition to the ultrasound diagnostic apparatus 1100, the ultrasound diagnostic system 1000 also includes an ultrasound probe 1001, a display 1008, and an operation console 1009. The following explains each piece of equipment included in the ultrasound diagnostic system 1000.

(1) Ultrasound Probe 1001

The ultrasound probe 1001 transmits a transmission wave, generated by an ultrasound transceiver 1002, into a body of a subject and receives reflected ultrasound that is reflected from within the subject. The ultrasound probe 1001 outputs the reflected ultrasound to the ultrasound transceiver 1002 as an echo signal.

The ultrasound probe 1001 for example includes a transducer column formed by a plurality of piezoelectric elements (not illustrated) arranged in a single direction (herein, referred to as a transducer arrangement direction) as a one dimensional array. The ultrasound probe 1001 converts a pulsed electrical signal (herein, referred to as a transmission ultrasound signal), supplied from the ultrasound transceiver 1002, to pulsed ultrasound (note that the ultrasound transceiver 1002 is explained further below). At the above time, the ultrasound probe 1001 transmits, toward a measurement target, an ultrasound beam formed by ultrasound emitted from the plurality of transducers. During transmission of the ultrasound beam, the ultrasound probe 1001 is positioned such that an outer surface thereof that is closest to the transducers is placed against skin surface of a subject. The ultrasound probe 1001 subsequently receives a plurality of reflected ultrasound waves from the subject and converts each of the reflected ultrasound waves into an electrical signal (herein, referred to as a reception ultrasound signal) through the transducers. The ultrasound probe 1001 outputs the reception ultrasound signal to the ultrasound transceiver 1002.

Through an ultrasound scan such as described above, in which the ultrasound probe 1001 transmits an ultrasound beam toward a region of the subject corresponding to the transducer column, and receives reflected ultrasound from the subject, an ultrasound image is acquired of a cross-section in the transducer arrangement direction and in a depth direction perpendicular thereto. An ultrasound image acquired through a single ultrasound scan is referred to as a frame. The term frame is used to express a unit of a group of signals necessary in order to construct a single cross-sectional image. A plurality of ultrasound image frames can be acquired by performing a plurality of ultrasound scans.

(2) Display 1008

The display 1008 is equipment for displaying an image and displays image output from a display controller on a screen. The display controller is explained further below. The display 1008 may for example be a liquid crystal display, a cathode ray tube, or an organic electroluminescence display.

(3) Operation Console 1009

The operation console 1009 is an input device that receives operational input of various settings and operations from an operator with respect to the ultrasound diagnostic apparatus 1100 and outputs the operational input to a control circuit 1010. The operator inputs information relating to, for example, a patient name, an examination date, operation or suspension of a screen, storage, and image quality adjustment. The inputted information is stored in a memory 1005.

More specifically, the operation console 1009 may for example be a keyboard, a trackball, or a touch panel. If the operation console 1009 is a touch panel, the operation console 1009 may be integrated with the display 1008. In such a configuration, the ultrasound diagnostic apparatus 1100 can be operated using the touch panel by performing an operation, such as a touch operation or a drag operation, with respect to an operation key displayed on the display 1008, in order to perform a setting or an operation with respect to the ultrasound diagnostic apparatus 1100.

The operation console 1009 may alternatively be a keyboard that has keys for performing various operations, or may be an operation panel that has buttons, levers, or the like for performing various operations. Further alternatively, the operation console 1009 may be a trackball, a mouse, or any other equipment for moving a cursor displayed on the display 1008. Note that the operation console 1009 may alternatively be a plurality of any of the aforementioned types of equipment, or may be a combination of different types of the aforementioned equipment.

(4) Ultrasound Diagnostic Apparatus 1100

Figure 2:
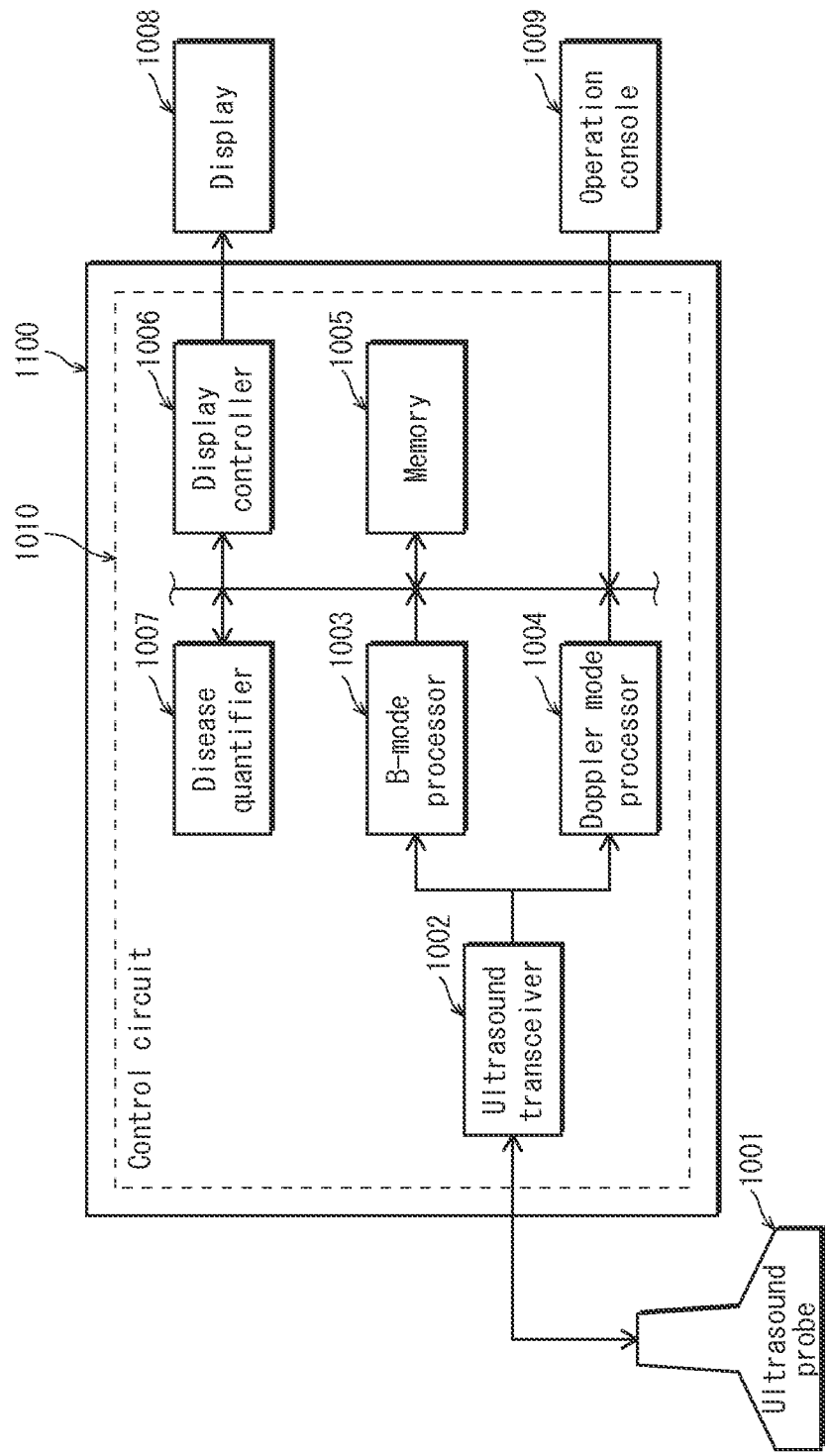
FIG. 2 is a block diagram illustrating internal configuration of the ultrasound diagnostic apparatus 1100.

The ultrasound diagnostic apparatus 1100 performs transmission and reception of ultrasound for ultrasound diagnosis through the ultrasound probe 1001, and performs imaging of reflected ultrasound signal which is received. The following explains internal configuration of the ultrasound diagnostic apparatus 1100. FIG. 2 is a functional block diagram illustrating internal configuration of the ultrasound diagnostic apparatus 1100. FIG. 2 illustrates the ultrasound diagnostic apparatus 1100 connected to the ultrasound probe 1001, the display 1008, and the operation console 1009.

As illustrated in FIG. 2, the control circuit 1010 in the ultrasound diagnostic apparatus 1100 includes the ultrasound transceiver 1002, a B-mode processor 1003, a Doppler mode processor 1004, the memory 1005, a display controller 1006, and a disease quantifier 1007. The ultrasound transceiver 1002, the B-mode processor 1003, the Doppler mode processor 1004, the display controller 1006, and the disease quantifier 1007 are for example each implemented as a hardware circuit such as a field programmable gate array (FPGA) or an application specific integrated circuit (ASIC). Alternatively, the aforementioned configuration elements may be implemented through software and a programmable device such as a central processing unit (CPU), a graphics processing unit (GPU), or a processor. Each of the aforementioned configuration elements may be single circuit component or may be a collection of circuit components. Further alternatively, a plurality of the aforementioned configuration elements may be combined as a single circuit component or as a collection of circuit components.

The ultrasound transceiver 1002 is connectable to the ultrasound probe 1001. The display controller 1006 is connectable to the display 1008. The control circuit 1010 is connectable to the operation console 1009 which receives input from the operator.

The above explains configuration of each piece of equipment included in the ultrasound diagnostic system 1000.

2. Configuration of Elements of Ultrasound Diagnostic Apparatus 1100

The following explains configuration of each of the elements included in the ultrasound diagnostic apparatus 1100.

(1) Ultrasound Transceiver 1002

The ultrasound transceiver 1002 is connected to the ultrasound probe 1001. The ultrasound transceiver 1002 performs a transmission process of supplying a pulsed transmission ultrasound signal to the ultrasound probe 1001, in order to cause the ultrasound probe 1001 to transmit an ultrasound beam. More specifically, the ultrasound transceiver 1002 for example includes a clock generation circuit, a pulse generation circuit, and a delay circuit. The clock generation circuit is a circuit that generates a clock signal used for determining transmission timing of the ultrasound beam. The pulse generation circuit is a circuit that generates a pulse signal for driving each of the transducers. The delay circuit is a circuit for performing ultrasound beamforming or ultrasound beam-steering by setting a delay time for ultrasound beam transmission with respect to each of the transducers and delaying ultrasound beam transmission from each of the transducers by the delay time set with respect thereto.

The ultrasound transceiver 1002 also performs a reception process of performing beamforming in an order of ultrasound scanning based on an echo signal input through the ultrasound probe 1001 and outputting an acoustic signal to the B-mode processor 1003 and the Doppler mode processor 1004.

Note that in the beamforming, the reception ultrasound signal acquired by the ultrasound probe 1001 is amplified and AD converted to an RF signal, and delay-and-sum is performed on the RF signal to generate the acoustic signal along the depth direction. The RF signal is for example formed from a plurality of signals in the transducer arrangement direction and in an ultrasound transmission direction perpendicular thereto, wherein each of the signals is an amplitude converted electrical signal of reflected ultrasound that is A/D converted to a digital signal. The acoustic signal is continuous data in the depth direction configuring the RF signal after the delay-and-sum process has been performed thereon.

The ultrasound transceiver 1002 successively repeats the transmission process and the reception process.

(2) B-mode Processor 1003

The B-mode processor 1003 generates a B-mode image signal based on the acoustic signal input from the ultrasound transceiver 1002. The B-mode image signal which is generated is temporarily stored in the memory 1005.

More specifically, the B-mode processor 1003 generates the B-mode image signal by performing processing such as envelope detection and logarithmic compression on the acoustic signal, thereby converting the acoustic signal to a luminance signal corresponding to strength of the acoustic signal, and by subsequently performing coordinate conversion on the luminance signal to an orthogonal coordinate system. The B-mode processor 1003 performs the aforementioned processing successively for each frame. Each time an ultrasound scan is performed, the B-mode processor 1003 outputs the B-mode image signal of the frame which is generated to the memory 1005. Also, as explained further below, the B-mode processor 1003 supplies the B-mode image signal to the display controller 1006. The display controller 1006 causes the display 1008 to display the B-mode image signal.

(3) Doppler Mode Processor 1004

The Doppler mode processor 1004 performs autocorrelation calculation with respect to the acoustic signal input from the ultrasound transceiver 1002 and extracts a Doppler component that forms source data of Doppler signals indicating temporal change in blood flow within the body. The Doppler mode processor 1004 generates a Doppler mode image signal that uses colors to expresses strength of blood flow information such as average velocity, variance, or power.

More specifically, the Doppler mode processor 1004 performs autocorrelation with respect to the acoustic signal and, after conversion to blood flow velocities, extracts a velocity component, indicating a blood flow component, through filtering. The Doppler mode processor 1004 generates the Doppler mode image signal by calculating an average velocity, variance, and power of the filtered blood flow component. Each time an ultrasound scan is performed, the Doppler mode processor 1004 outputs the Doppler mode image signal which is generated to the memory 1005. Also, as explained further below, the Doppler mode processor 1004 supplies the Doppler mode image signal to the display controller 1006. The display controller 1006 causes the display 1008 to display the Doppler mode image signal.

(4) Memory 1005

The memory 1005 is a storage device that each time an ultrasound scan is performed, receives a B-mode image signal and a Doppler mode image signal of a frame which is generated, and temporarily stores the B-mode image signal and the Doppler mode image signal therein. The memory 1005 also stores diseases score calculated by the disease quantifier 1007, which is explained further below. The memory 1005 is random access memory (RAM) including static random access memory (SRAM) and dynamic random access memory (DRAM) using semiconductor memory. Alternatively, the memory 1005 may for example be a hard disk drive, an optical disk drive, or a magnetic storage device. Note that in the present description, the term ultrasound image signal refers to a signal that includes a B-mode image signal and a Doppler mode image signal.

(5) Disease Quantifier 1007

The disease quantifier 1007 quantifies disease activity of rheumatoid arthritis through analysis of B-mode image signals and Doppler mode image signals stored in the memory 1005. A method used for quantifying disease activity is explained further below. Quantification results are stored in the memory for the ultrasound image signal of each frame.

(6) Display Controller 1006

The display controller 1006 creates a display screen based, for example, on a B-mode image signal and a Doppler mode image signal stored in the memory 1005. The display controller 1006 superimposes information on the display screen such as an examiner name, a patient name, time information, ultrasound diagnostic apparatus settings, and scores calculated by the disease quantifier 1007. The display controller 1006 causes the display 1008, which is connected externally thereto, to display the display screen. Note that alternatively the ultrasound diagnostic apparatus 1100 may partially or completely include the ultrasound probe 1001, the operation console 1009, and the display 1008 as necessary.

3. Detailed Configuration of Disease Quantifier 1007

Figure 3:
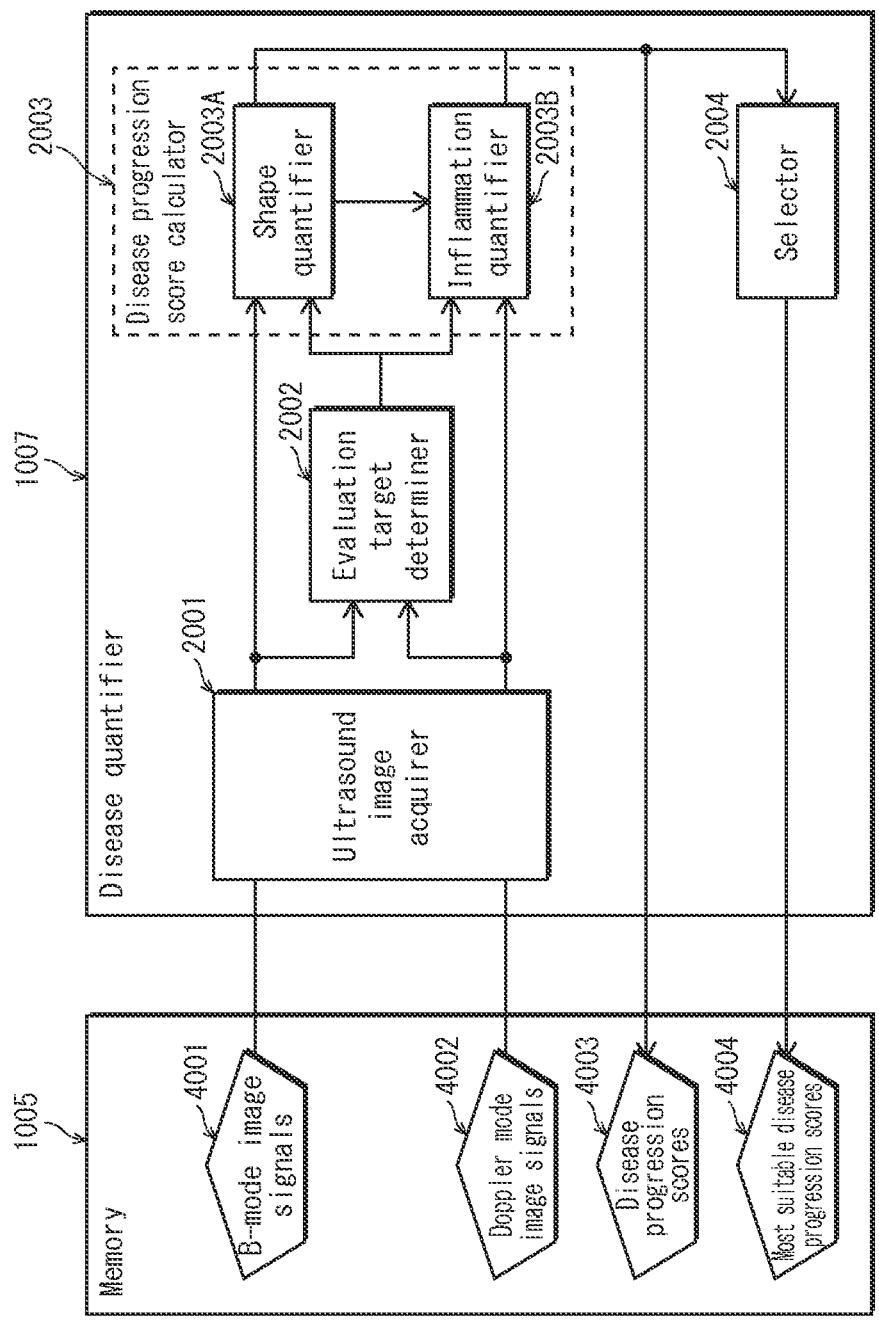
FIG. 3 is a block diagram illustrating a disease quantifier 1007 included in the ultrasound diagnostic apparatus 1100.

The following explains detailed configuration of the disease quantifier 1007 with reference to the drawings. FIG. 3 is a block diagram of the disease quantifier 1007.

The disease quantifier 1007 includes an ultrasound image acquirer 2001, an evaluation target determiner 2002, a disease progression score calculator 2003, and a selector 2004. The disease progression score calculator 2003 includes a shape quantifier 2003A and an inflammation quantifier 2003B. The disease quantifier 1007 receives B-mode image signals 4001 and Doppler mode image signals 4002 stored in the memory 1005 as input. The disease quantifier 1007 outputs, to the memory 1005, disease progression scores 4003 indicating disease activity and a most suitable disease progression score 4004, which is for example a maximum value among the disease progression scores 4003.

(1) Ultrasound Image Acquirer 2001

The ultrasound image acquirer 2001 reads a B-mode image signal 4001 and a Doppler mode image signal 4002 of each of a plurality of frames for which B-mode image signals 4001 and Doppler mode image signals 4002 are stored in the memory 1005.

(2) Evaluation Target Determiner 2002

The evaluation target determiner 2002 receives a B-mode image signal 4001 and a Doppler mode image signal 4002 outputted from the ultrasound image acquirer 2001 as input. The evaluation target determiner 2002 analyzes the B-mode image signal 4001 and the Doppler mode image signal 4002 and thereby determines whether the operator has used appropriate procedural technique when acquiring the ultrasound image of the corresponding frame. The evaluation target determiner 2002 outputs results of the aforementioned determination to the shape quantifier 2003A and the inflammation quantifier 2003B.

Figure 4:
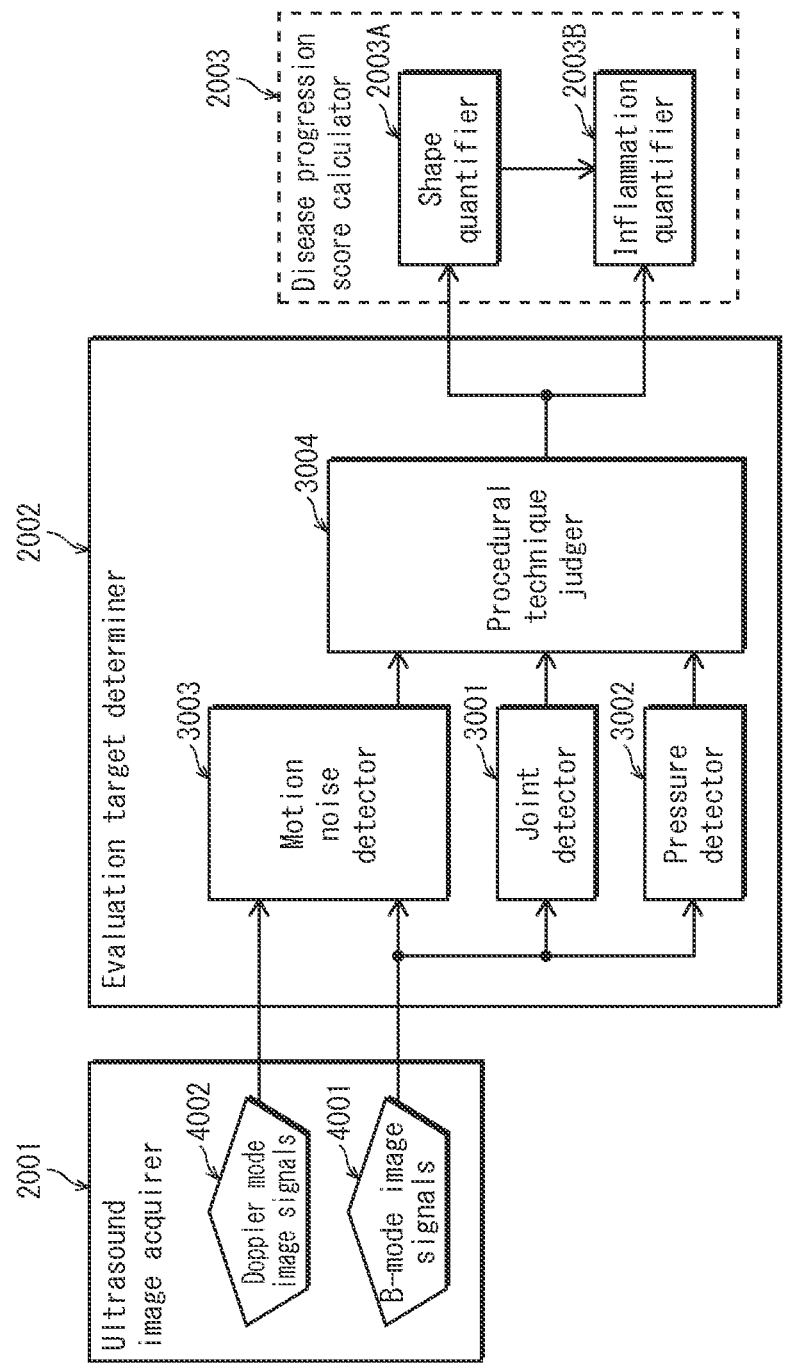
FIG. 4 is a block diagram illustrating an evaluation target determiner 2002 included in the ultrasound diagnostic apparatus 1100.

The following explains detailed configuration of the evaluation target determiner 2002 with reference to the drawings. FIG. 4 is a block diagram of the evaluation target determiner 2002. As illustrated in FIG. 4, the evaluation target determiner 2002 includes a joint detector 3001, a pressure detector 3002, a motion noise detector 3003, and a procedural technique judger 3004.

(i) Joint Detector 3001

The joint detector 3001 receives the B-mode image signal 4001 output from the ultrasound image acquirer 2001 as input and judges, for the ultrasound image signal of the corresponding frame, whether the ultrasound image signal includes a target image section depicting a joint. The joint detector 3001 outputs a judgment result indicating either "joint present" or "joint not present" to the procedural technique judger 3004. A method used for performing the aforementioned judgment is explained further below.

(ii) Pressure Detector 3002

The pressure detector 3002 receives the B-mode image signal 4001 output from the ultrasound image acquirer 2001 as input and judges, from an image of the B-mode image signal 4001, whether the ultrasound image signal of the corresponding frame has been acquired while the ultrasound probe is not applying pressure against the body surface of the subject. The pressure detector 3001 outputs a judgment result indicating either "pressure applied" or "pressure not applied" to the procedural technique judger 3004. A method used for performing the aforementioned judgment is explained further below.

(iii) Motion Noise Detector 3003

The motion noise detector 3003 receives the B-mode image signal 4001 and the Doppler mode image signal 4002 output from the ultrasound image acquirer 2001 as input and judges whether the Doppler mode image signal 4002 included in the ultrasound image signal of the corresponding frame is caused by motion noise. The motion noise detector 3003 outputs a judgment result indicating either "motion noise present" or "motion noise not present" to the procedural technique judger 3004. A method used for performing the aforementioned judgment is explained further below.

(iv) Procedural Technique Judger 3004

The procedural technique judger 3004 receives the respective judgment results of the joint detector 3001, the pressure detector 3002, and the motion noise detector 3003 as input. The procedural technique judger 3004 judges that the ultrasound image signal of the corresponding frame is acquired using appropriate procedural technique when the procedural technique judger 3004 receives a judgment result of "joint present". Alternatively, the procedural technique judger 3004 may judge that the ultrasound image signal of the corresponding frame is acquired using appropriate procedural technique when the procedural technique judger 3004 receives a judgment result of "joint present", and also receives at least one of a judgment result of "pressure not applied" and a judgment result of "motion noise not present". In the above situation, the procedural technique judger 3004 outputs a judgment result indicating "perform quantification" to the shape quantifier 2003A and the inflammation quantifier 2003B. In other situations, the procedural technique judger 3004 outputs a judgment result indicating "suspend quantification".

(3) Shape Quantifier 2003A

Returning to explanation of FIG. 3, the following explains configuration of the disease progression score calculator 2003. As previously explained, the disease progression score calculator 2003 includes the shape quantifier 2003A and the inflammation quantifier 2003B.

First, configuration of the shape quantifier 2003A is explained. The shape quantifier 2003A receives the B-mode image signal 4001 output from the ultrasound image acquirer 2001 and the judgment result output from the evaluation target determiner 2002 as input. When the judgment result is "suspend quantification", the shape quantifier 2003A invalidates a disease progression score without performing quantification. On the other hand, when the judgment result is "perform quantification", the shape quantifier 2003A calculates a disease progression score based, for example, on size of an image section depicting a joint in the B-mode image signal 4001 or a luminance pattern of an image section depicting bone in the B-mode image signal 4001. The disease progression score calculated by the shape quantifier 2003A is referred to as a swelling score (GS; Grey Scale). The swelling score is stored in the memory 1005. A method for calculating the aforementioned swelling score is explained further below.

(4) Inflammation Quantifier 2003B

Next, configuration of the inflammation quantifier 2003B is explained. The inflammation quantifier 2003B receives the Doppler mode image signal 4002 output from the ultrasound image acquirer 2001, the judgment result output from the evaluation target determiner 2002, and information relating to an articular cavity output from the shape quantifier 2003A as input. When the judgment result is "suspend quantification", the inflammation quantifier 2003B invalidates a disease progression score without performing quantification. On the other hand, when the judgment result is "perform quantification", the inflammation quantifier 2003B calculates a disease progression score based on size of a region for which Doppler signals are detected, in the Doppler mode image signal 4003, in an image section 6 depicting an articular cavity, which is located between a bone surface and an image section 5 depicting an articular capsule. The disease progression score calculated by the inflammation quantifier 2003B is referred to as an inflammation score (PD; Power Doppler). The inflammation score is stored in the memory 1005. A method used for calculating the aforementioned inflammation score is explained further below.

(5) Selector 2004

The selector 2004 receives, as input, disease progression scores (swelling scores and inflammation scores) that have been stored in the memory 1005 after calculation by the shape quantifier 2003A and the inflammation quantifier 2003B. The selector 2004 selects at least one most suitable disease progression score in accordance with a predetermined numerical process. For example, the selector 2004 may select a maximum value of disease progression scores for a plurality of frames as the most suitable disease progression score. Alternatively, the selector 2004 may select a median value or a mean value of the disease progression scores for the plurality of frames as the most suitable disease progression score. The selector 2004 outputs the at least one most suitable disease progression score to the memory 1005, thereby storing the most suitable disease progression score in the memory 1005.

In a situation in which the maximum value of the disease progression scores for the plurality of frames is selected as the most suitable disease progression score, the selector 2004 may receive the disease progression scores calculated by the shape quantifier 2003A and the inflammation quantifier 2003B as input, store a maximum value for each of the two types of disease progression score, and output the maximum value to the memory 1005 as the most suitable disease progression score once disease progression scores for all of the frames have been input to the selector 2004.

<Operation>

1. Operation of Ultrasound Diagnostic Apparatus 1100

The following explains operation of the ultrasound diagnostic apparatus 1100 when performing an examination for rheumatoid arthritis, using finger joints as an example. In examination of the finger joints for rheumatoid arthritis, examination is performed with respect to a selected joint among all of the finger joints. During examination of the finger joint, ultrasound scans are performed with respect to a plurality of different cross-sections of the finger joint.

Figure 5:
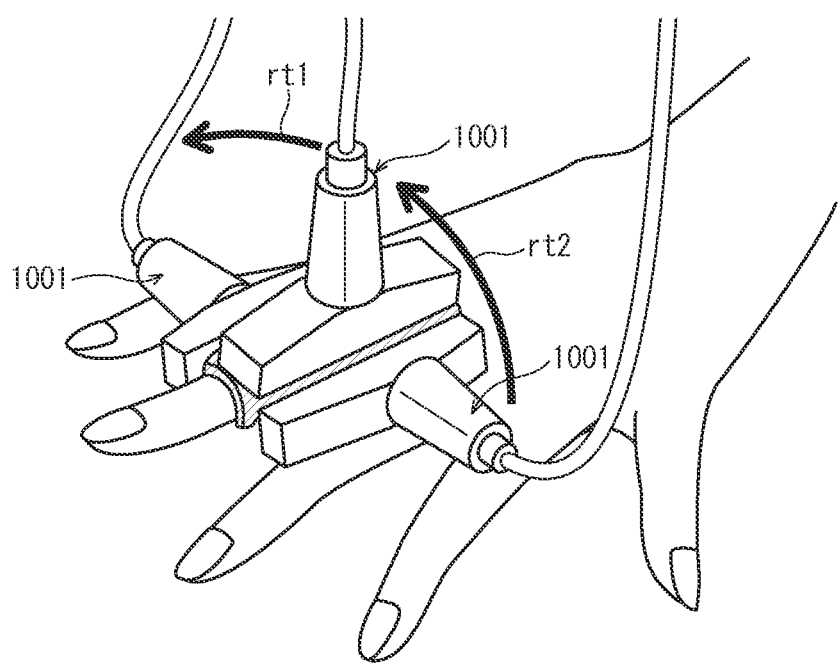
FIG. 5 is a schematic diagram illustrating examination of rheumatoid arthritis in a finger joint.

FIG. 5 is a schematic diagram illustrating examination of a finger joint for rheumatoid arthritis using the ultrasound diagnostic apparatus 1100. As illustrated in FIG. 5, the ultrasound probe 1001 is positioned along the finger joint such that the transducer column is orientated in a direction parallel to a longitudinal direction of the finger. In the state described above, the ultrasound probe 1001 is rotated about the finger as a rotational axis as shown by arrows rt1 and rt2 in FIG. 5. Through rotation of the ultrasound probe 1001, a plurality of ultrasound scans are performed at different inclination angles relative to the finger joint, thereby capturing a plurality of ultrasound images of the finger joint. Diagnosis of rheumatoid arthritis is performed with respect to the finger joint based on the ultrasound images which are acquired.

(1) Outline of Process for Disease Progression Score Calculation

Figure 6:
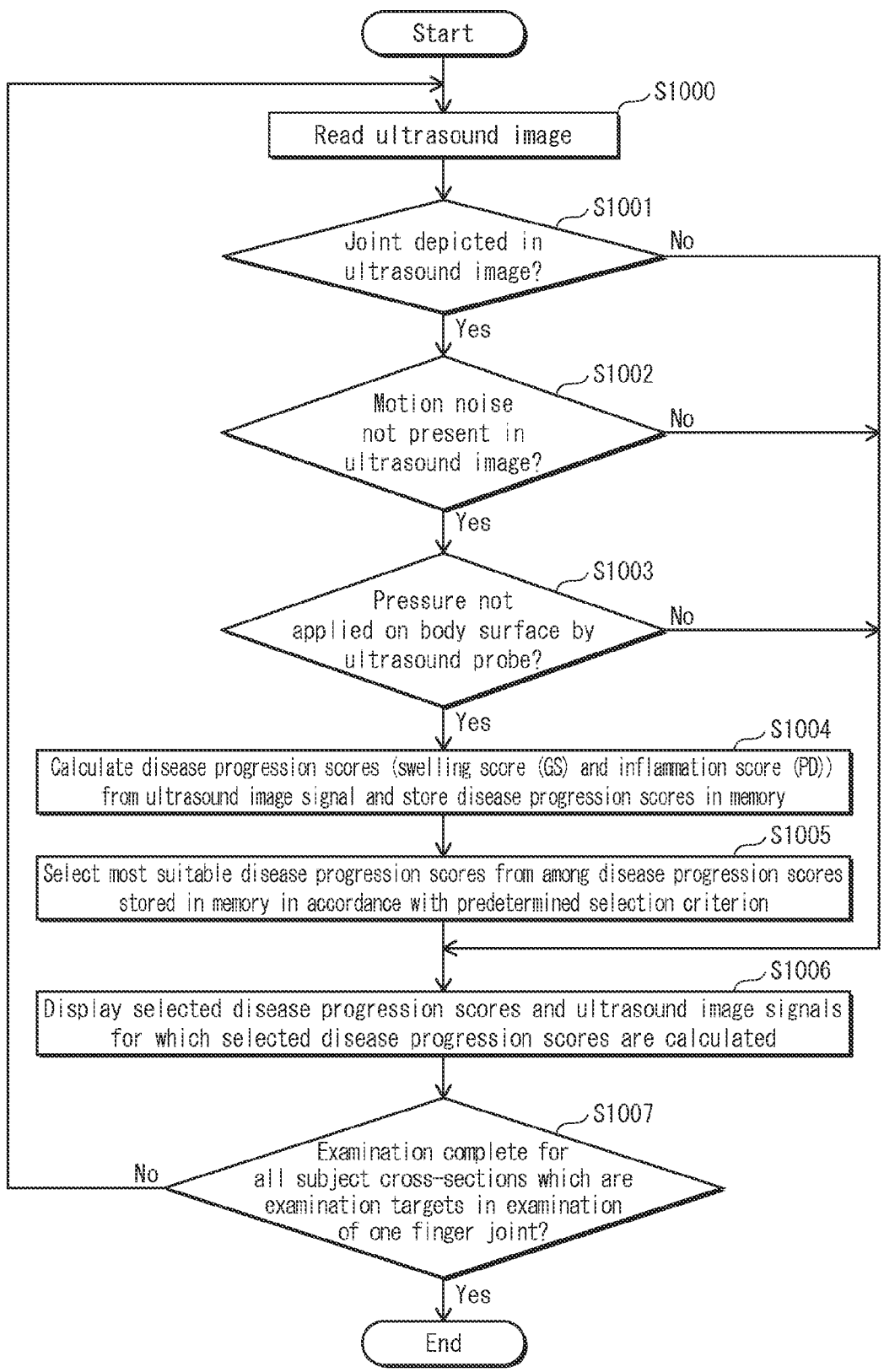
FIG. 6 is a flowchart illustrating a process for disease progression score calculation in the ultrasound diagnostic apparatus 1100.

FIG. 6 is a flowchart illustrating a process for disease progression score calculation in the ultrasound diagnostic apparatus 1100 relating to the present embodiment.

(i) Evaluation Target Frame Determination

In step S1000, the ultrasound image acquirer 2001 reads a B-mode image signal 4001 and a Doppler mode image signal 4002 of a frame from among B-mode image signals 4001 and Doppler mode image signals 4002 of a plurality of frames stored in the memory 1005.

Next, in step S1001 the joint detector 3001 receives the B-mode image signal 4001 as input and judges, for the ultrasound image signal of the frame, whether the ultrasound image signal includes a target image section depicting a joint. When the ultrasound image signal includes the target image section depicting the joint, the process proceeds to step S1002, and when the ultrasound image signal does not include the target image section, the process proceeds to step S1006.

In step S1002, the motion noise detector 3003 judges whether the Doppler mode image signal 4002 included in the ultrasound image of the frame is caused by motion noise. When the Doppler mode image signal 4002 is not caused by motion noise, the process proceeds to step S1003, and when the Doppler mode image signal 4002 is caused by motion noise, the process proceeds to step S1006.

Next, in step S1003 the pressure detector 3002 judges whether the ultrasound probe 1001 is not applying pressure against the body surface of the subject. When the ultrasound probe 1001 is not applying pressure against the body surface of the subject, the process proceeds to step S1004, and when the ultrasound probe 1001 is applying pressure, the process proceeds to step S1006.

In other words, the procedural technique judger 3004 judges that an ultrasound image signal of a target frame has been acquired using appropriate procedural technique when a judgment result of step 1001 in FIG. 6 is "joint present", a judgment result of step S1002 is "motion noise not present", and a judgment result of step S1003 is "pressure not applied", and thus outputs a judgment result indicating "perform quantification" to the shape quantifier 2003A and the inflammation quantifier 2003B.

(ii) Disease Progression Score Calculation

In step S1004, the disease progression score calculator 2003 calculates disease progression scores. The shape quantifier 2003A outputs a swelling score to the memory 1005 and the memory 1005 stores the swelling score therein. The inflammation quantifier 2003B outputs an inflammation score to the memory 1005 and the memory 1005 stores the inflammation score therein.

(iii) Disease Progression Score Selection

In step S1005, the selector 2004 receives disease progression scores (swelling scores and inflammation scores) stored in the memory 1005 as input and selects at least one most suitable disease progression score in accordance with a predetermined numerical process.

When the process of steps S1000 to S1005 has been performed at least twice for the same finger joint as an examination target, the selector 2004 selects the most suitable disease progression score, in accordance with the predetermined numerical process, from among a plurality of disease progression scores stored in the memory 1005 that have been obtained from ultrasound image signals of a plurality of frames for which examination has been performed.

Through the above, disease activity is evaluated based on the most suitable disease progression score, which is selected in accordance with the predetermined numerical process, and based on an ultrasound image signal of a frame for which the most suitable disease progression score was calculated. Therefore, disease activity can be evaluated without dependence on procedural technique or subjective judgments of the examiner during examination.

Note that when the process of steps S1000 to S1005 is performed for a first time with respect to a target finger joint, only a disease progression score acquired from the ultrasound image signal of one frame is stored in the memory. In such a situation, the selector 2004 selects the one disease progression score that is stored in the memory 1005.

(iv) Disease Progression Score Display

In step S1006, the display controller 1006 creates a display screen using the disease progression scores stored in the memory 1005 and the most suitable disease progression score selected in accordance with the predetermined numerical process in step S1005, and causes the display 1008 connected externally thereto to display the display screen. Alternatively, the display controller 1006 may create a display screen using the most suitable disease progression score selected in step 51005 and the ultrasound image signal of the frame for which the most suitable disease progression score was calculated, and may cause the display 1008 to display the display screen.

(v) Completion of Examination

In step S1007, a judgment is performed as to whether evaluation has been completed for ultrasound images of all frames to be used in examination of the finger joint. Once evaluation has been completed for the ultrasound images of all of the frames, the process for disease progression score calculation is complete. On the other hand, when there is an ultrasound image of a frame for which evaluation is yet to be performed, the process for disease progression score calculation returns to step S1001.

The following explains operation of the ultrasound diagnostic apparatus 1100 during each of the aforementioned steps.

(2) Process for Joint Detection

A process used by the joint detector 3001 is explained with reference to the drawings.

Figure 7:
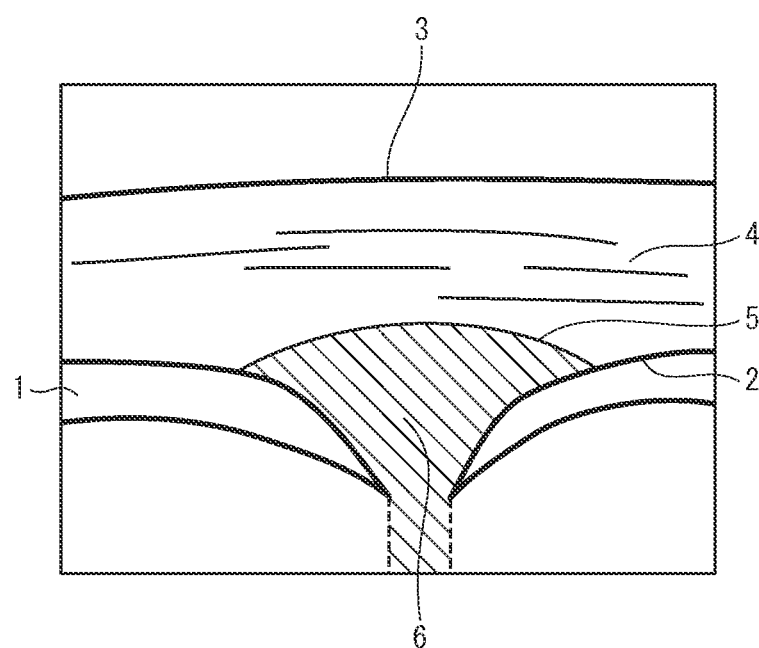
FIG. 7 is a schematic diagram illustrating an ultrasound image captured of a finger joint as a measurement target.

FIG. 7 is a schematic diagram illustrating an ultrasound image which is captured with respect to a finger joint as a measurement target using the ultrasound diagnostic apparatus 1100. The ultrasound image illustrated in FIG. 7 is a B-mode image that is acquired by orientating the transducer column in a direction parallel to the longitudinal direction of the finger and performing an ultrasound scan of the finger joint. As illustrated in FIG. 7, the B-mode image depicts the finger joint and includes image sections 1 and 2 depicting bone, an image section 3 depicting skin, an image section 4 depicting tendon, and an image section 5 depicting an articular capsule. Bone, skin, and tendon are relatively hard tissues. Therefore, the image sections 1 and 2 depicting bone, the image section 3 depicting skin, and the image section 4 depicting tendon are each rendered with a high luminance in the ultrasound image. The majority of incident ultrasound is reflected off of a surface of bone. Therefore, only a section corresponding to bone cortex at the surface is rendered with a high luminance and an internal section of bone is not rendered. The image section 6 depicting the articular cavity is rendered with a relatively low luminance compared to the image sections 1 and 2 depicting bone, and the image section 3 depicting skin. Also, an image section corresponding to a synovial membrane or cartilage is rendered with a luminance value of approximately zero, and thus is not displayed.

Therefore, in an ultrasound image of a joint, tissues which are rendered with relatively high luminance are skin, tendons, and bone surfaces. Through detection of the image section 5 depicting the articular capsule and the image sections 1 and 2 depicting bone from the B-mode image signal, the joint detector 3001 of the ultrasound diagnostic apparatus 1100 identifies an image section 6 depicting an articular cavity, which is surrounded by the aforementioned detected image sections. The joint detector 3001 also identifies an image section depicting the joint, which is formed from the image section 5 depicting the articular capsule, the image sections 1 and 2 depicting bone, and the image section 6 depicting the articular cavity.

Figure 8:
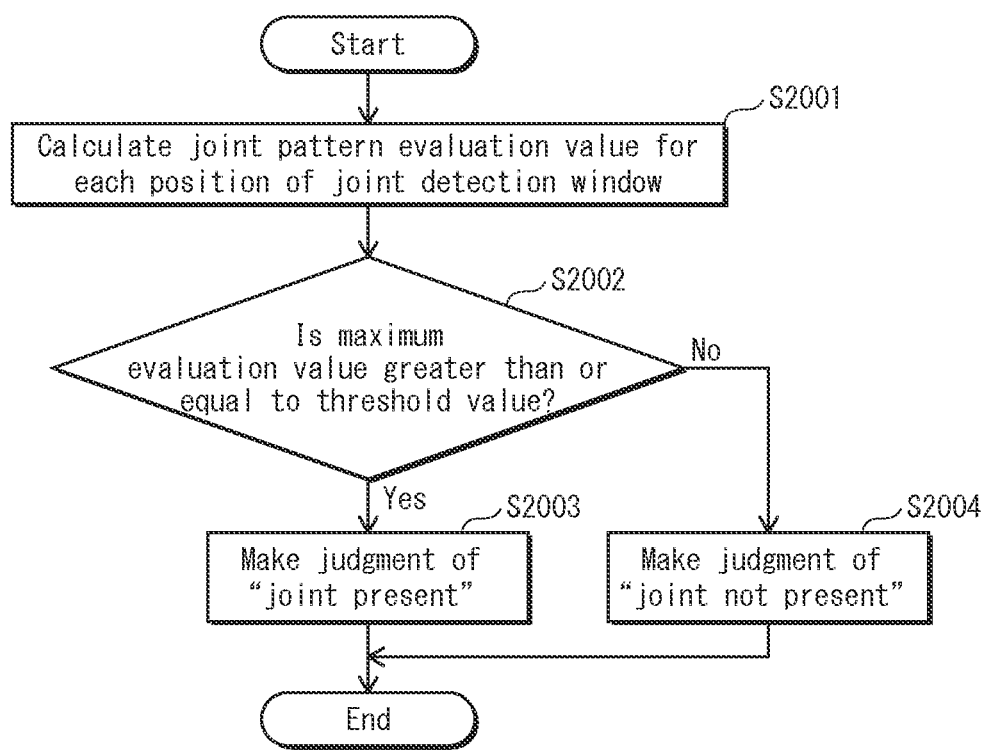
FIG. 8 is a flowchart illustrating operation during a process for joint detection in the ultrasound diagnostic apparatus 1100.

FIG. 8 is a flowchart illustrating operation during the process for joint detection.

The joint detector 3001 acquires, through the ultrasound image acquirer 2001, a B-mode image signal of a single frame stored in the memory 1005 and performs a search for an image section depicting a joint.

First, in step S2001 the joint detector 3001 calculates, for each position of a joint detection window 302, an evaluation value indicating similarity to a joint pattern and searches for a position of the joint detection window 302 having a maximum evaluation value. The search for the position of the joint detection window 302 having the maximum evaluation value is performed as described below.

Figure 9A:
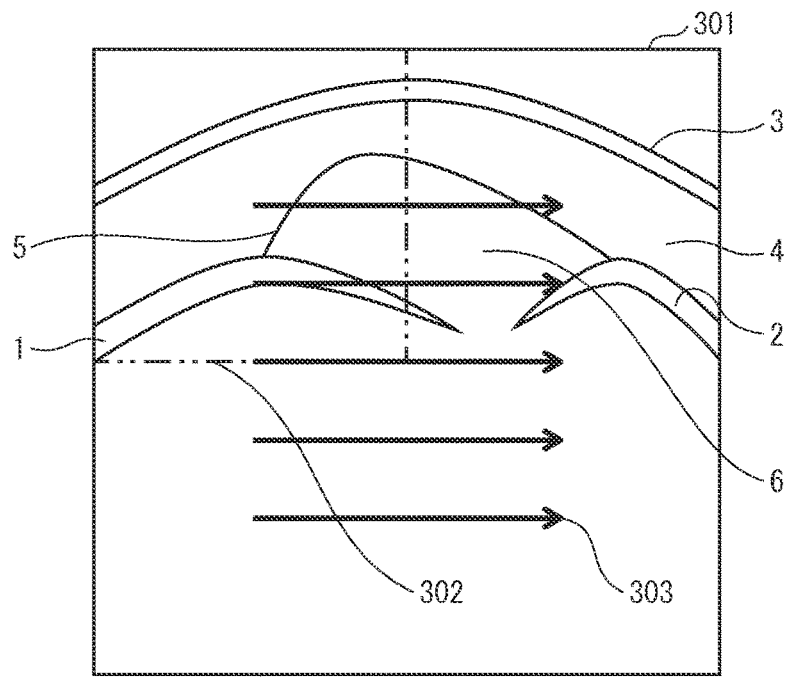
FIGS. 9A and 9B are schematic diagrams illustrating a joint detection window used in a process of joint searching.
Figure 9B:
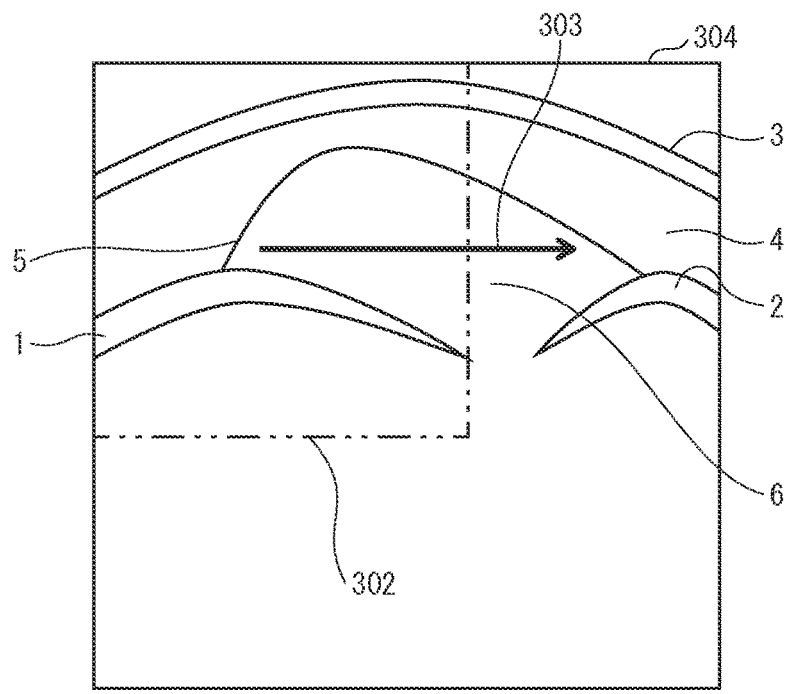

FIGS. 9A and 9B are schematic diagrams illustrating a joint detection window used in a process for joint searching. The joint detection window 302 is set in a B-mode image 301. A search process is performed with respect to the entire B-mode image 301 by shifting the joint detection window 302 in a direction of a scan line 303 and performing a search process with respect to a section of the B-mode image 301 included within the joint detection window 302 at each position thereof. Also, in order that detection can be performed for joints of various sizes, a B-mode image 304 may be created by either enlarging or reducing the B-mode image 301, and the search process may be performed on the B-mode image 304 using the joint detection window 302.

FIG. 10 is provided in order to facilitate explanation of operation of the ultrasound diagnostic apparatus 1100 during the process for joint searching. As illustrated in FIG. 10, a template matching method is used in the process for joint searching relating to the present embodiment. According to the template matching method, the joint detection window 302 is set in the B-mode image 301 and an evaluation value indicating similarity to a joint pattern is calculated for an image section within the joint detection window 302. The evaluation value is calculated by comparing the image section to a template 305 depicting a typical image pattern of a joint, and calculating a degree of similarity therebetween (for example, an error value or a correlation value). The template 305 may for example be a B-mode image depicting an average image pattern of a joint. The joint detection window 302 is shifted in the direction indicated by the scan line 303 and the search process is performed for a section of the B-mode image within the joint detection window 302 at each position thereof. The aforementioned process is repeated while shifting the joint detection window 302 such that the joint detection window 302 is scanned across the entire B-mode image 301, and an image section is identified which is included within the joint detection window 302 at a position thereof having a maximum evaluation value.

Figure 11:
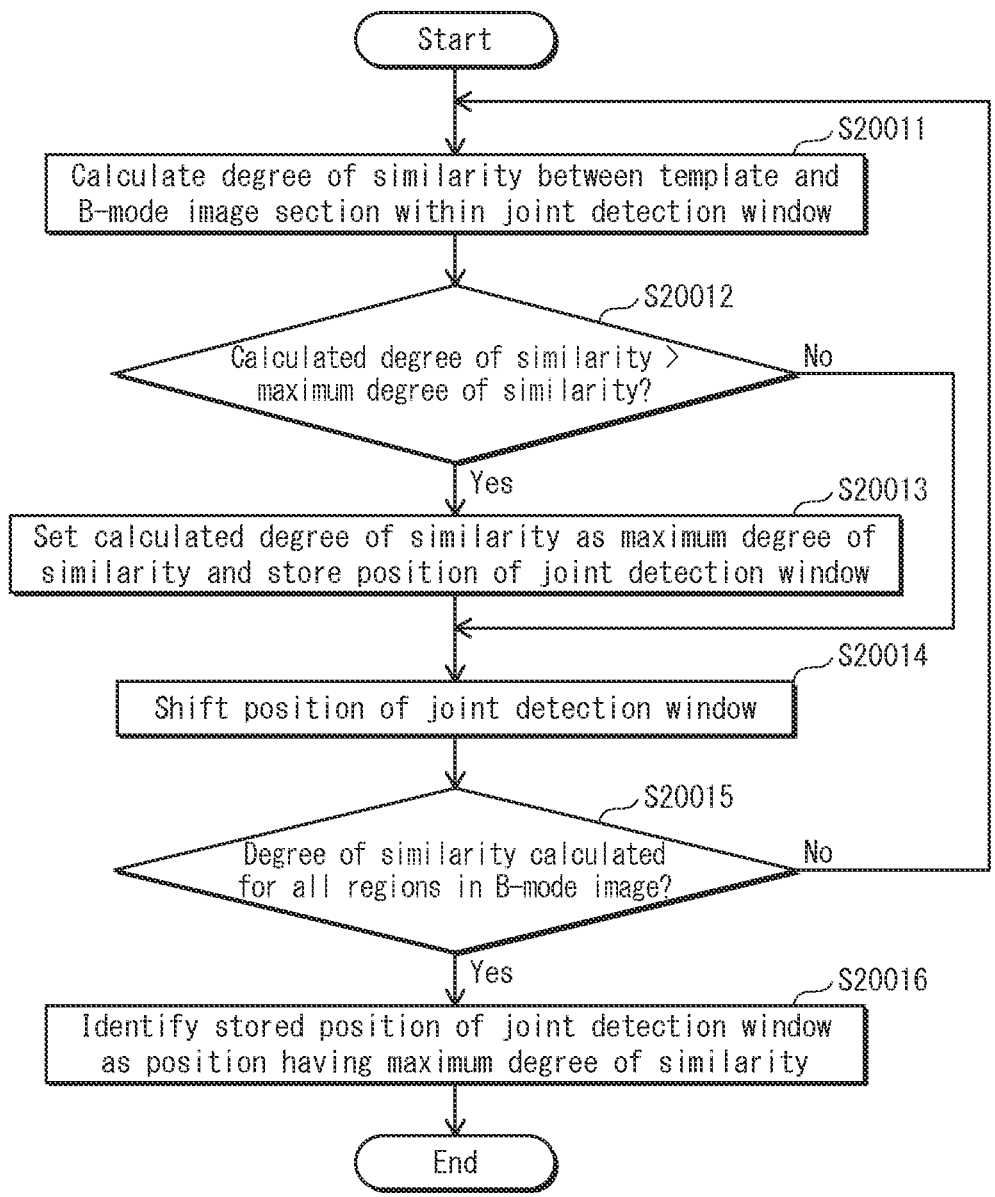
FIG. 11 is a flowchart illustrating details of a process for joint detection using a template matching method in the ultrasound diagnostic apparatus 1100.

FIG. 11 is a flowchart illustrating details of a process for joint detection performed according to the template matching method. The flowchart in FIG. 11 illustrates one example of the process in step S2001 of FIG. 8. As illustrated in FIG. 10, a top left corner of the B-mode image 301 is set as an initial position of the joint detection window 302. The joint detector 3001 calculates a degree of similarity between the template 305, depicting a typical image pattern of a joint, and a section of the B-mode image within the joint detection window 302 (step S20011). The joint detector 3001 calculates the degree of similarity by calculating an error value for each pixel in the joint detection window 302 using luminance information for the section of the B-mode image within the joint detection window 302 and luminance information for the template 305, and calculating a sum total of error values for all of the pixels in the joint detection window 302. Alternatively, the joint detector 3001 may calculate the degree of similarity by calculating a correlation value between the luminance information for the section of the B-mode image within the joint detection window 302 and the luminance information for the template 305.

When the degree of similarity is calculated with respect to the initial position of the joint detection window 302, the joint detector 3001 sets the degree of similarity as a maximum value, and when the degree of similarity is calculated with respect to any other position of the joint detection window 302, the joint detector 3001 compares the degree of similarity which is calculated to a previously set maximum value (step S20012).

When the degree of similarity which is calculated is larger than the maximum value, the joint detector 3001 sets the calculated degree of similarity as the maximum value and stores the position of the joint detection window 302 (step S20013). In all other situations, the process proceeds to step S20014.

Next, the joint detector 3001 gradually shifts position of the joint detection window 302 in the B-mode image 301 in an X direction or a Y direction as illustrated by the scan line 303, and calculates a degree of similarity at each position of the joint detection window 302. A search range is the entirety of the B-mode image 301. Once the joint detector 3001 has calculated a degree of similarity for all regions of the B-mode image 301 (step S20015), the joint detector 3001 identifies the position of the joint detection window 302 stored during step S20013 as a position of the joint detection window 302 having a maximum degree of similarity (step S20016).

Figure 12:
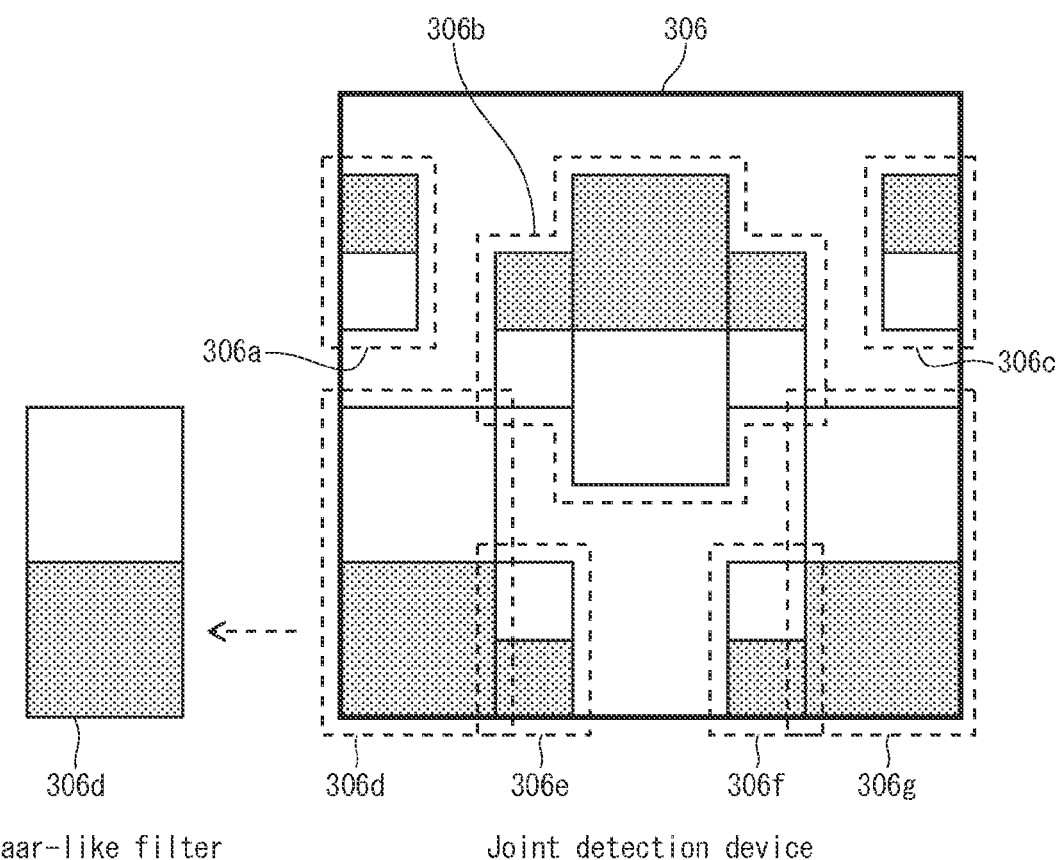
FIG. 12 is a schematic diagram illustrating one example of a joint detection device that uses machine learning.

The evaluation value is not limited to being calculated using the template matching method described above. For example, alternatively a joint pattern/non-joint pattern recognition device may use a Haar-like filter that is obtained through machine learning. FIG. 12 is a schematic diagram illustrating one example of a joint searching device that uses machine learning. In a process for joint searching that uses machine learning, the same process flow as illustrated in FIG. 11 is performed using a joint detector 306 formed from a plurality of Haar-like filters 306a-306g, instead of using the template 305 depicting the typical image pattern of a joint. Each of the Haar-like filters 306a-306g is a filter for detecting luminance changes. Sensitivity and weighting with respect to position, size, and luminance change within a joint detection window can be obtained through a machine learning technique such as adaptive boosting (AdaBoost). An output value of each of the filters is calculated when identifying a joint position in step S20016 and a degree of similarity is calculated as a linear combination of the output values of the filters and the weightings obtained through the machine learning.

Returning to explanation of FIG. 8, in step S2002 the joint detector 3001 compares the maximum evaluation value to a threshold value. When the maximum evaluation value is greater than or equal to the threshold value, the joint detector 3001 makes a judgment result of "joint present" (step S2003), and when the maximum evaluation value is less than the threshold value, the joint detector 3001 makes a judgment result of "joint not present" (step S2004). The joint detector 3001 outputs the judgment result to the procedural technique judger 3004. The joint detector 3001 outputs information to the procedural technique judger 3004 indicating a position of the joint detection window 302 corresponding to the maximum evaluation value.

(3) Process for Motion Noise Detection

In step S1002 of FIG. 6, the motion noise detector 3003 judges whether a Doppler mode image signal included in an ultrasound image signal of a frame is caused by motion noise. In the present description, motion noise refers to Doppler signals that are generated due to the operator causing a large movement of the ultrasound probe 1001, and thus are Doppler signals that are not generated due to blood flow.

In a situation in which a Doppler signal does not appear in the Doppler mode image signal of the frame, the motion noise detector 3003 makes a judgment result of "image noise not present".

When Doppler signals appear in the ultrasound image of a frame, presence of motion noise is judged using:

(1) luminance change values for each pixel between a B-mode image signal of the frame and a B-mode image signal of a directly preceding frame (herein, referred to as an inter-frame luminance differences);

(2) a proportion of surface area occupied by a region (herein, referred to as a Doppler signal detection region) in which the Doppler signals appear in the B-mode image signal of the frame; and (3) a proportion of surface area of a high luminance region in the B-mode image signal of the frame that is occupied by the Doppler signal detection region.

Figure 13:
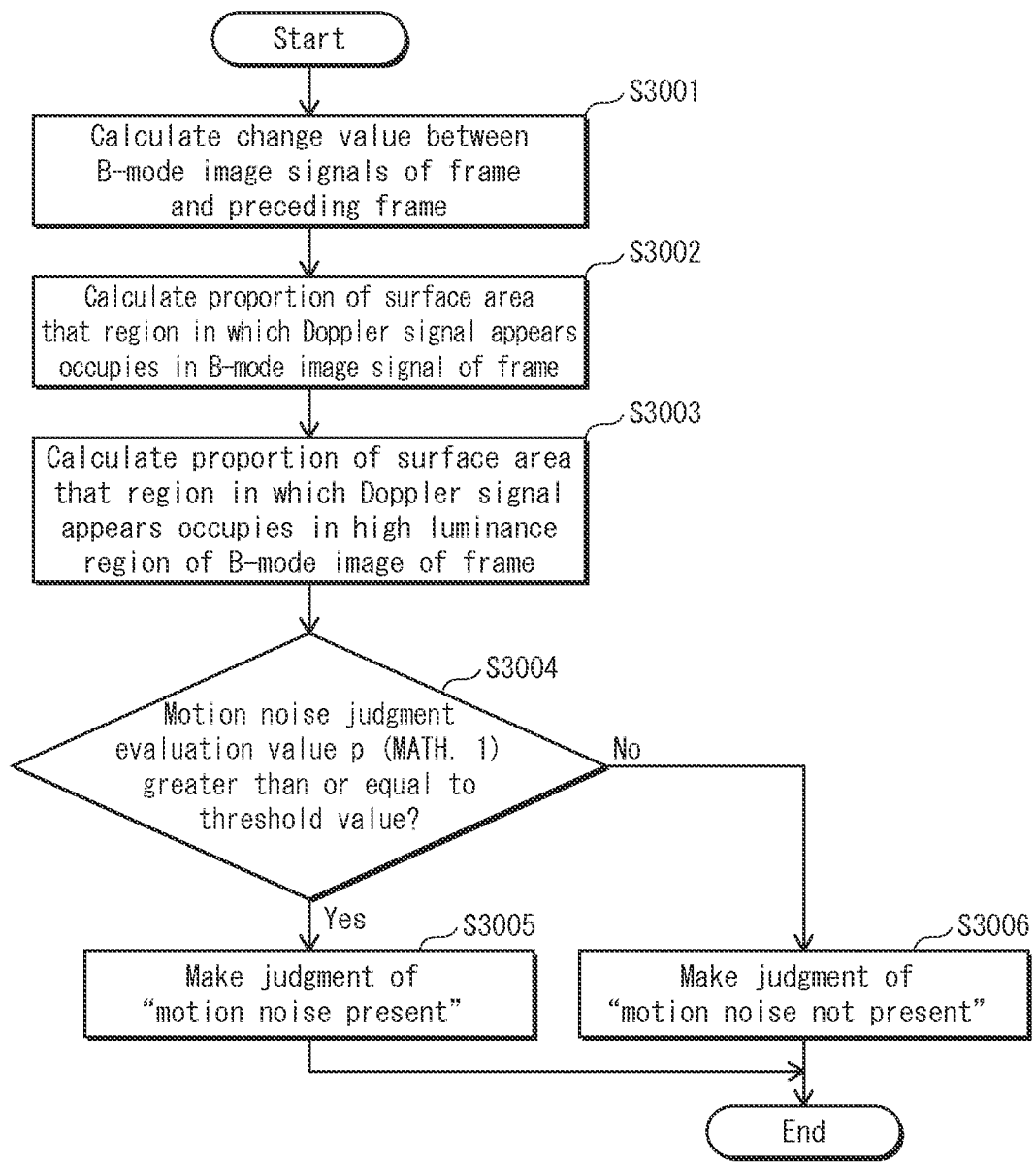
FIG. 13 is a flowchart illustrating a process for motion noise detection in the ultrasound diagnostic apparatus 1100.

FIG. 13 is a flowchart of motion noise detection.

First, in step S3001 the motion noise detector 3003 calculates a luminance change value for each pixel between the B-mode image signal of the frame and the B-mode image signal of the directly preceding frame. The luminance change values are inter-frame correlation values that decrease when the operator moves the ultrasound probe by a large amount. Instead of the correlation values, alternatively the sum of pixel value errors may be used.

Next, in step S3002 the motion noise detector 3003 calculates a proportion of surface area of the B-mode image signal of the frame which is occupied by a Doppler signal detection region. More specifically, the motion noise detector 3003 calculates a number of pixels for which a Doppler signal appears as a fraction of a total number of pixels in the Doppler mode image signal of the frame.

Figure 14A:
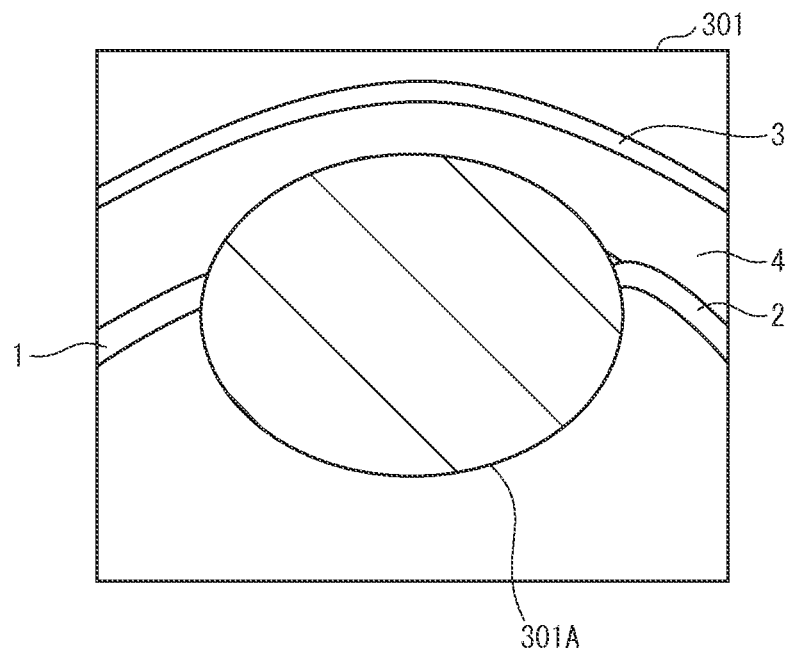
FIGS. 14A and 14B are schematic diagrams, each illustrating one example of a situation in which motion noise occurs in a B-mode image signal of a frame.
Figure 14B:
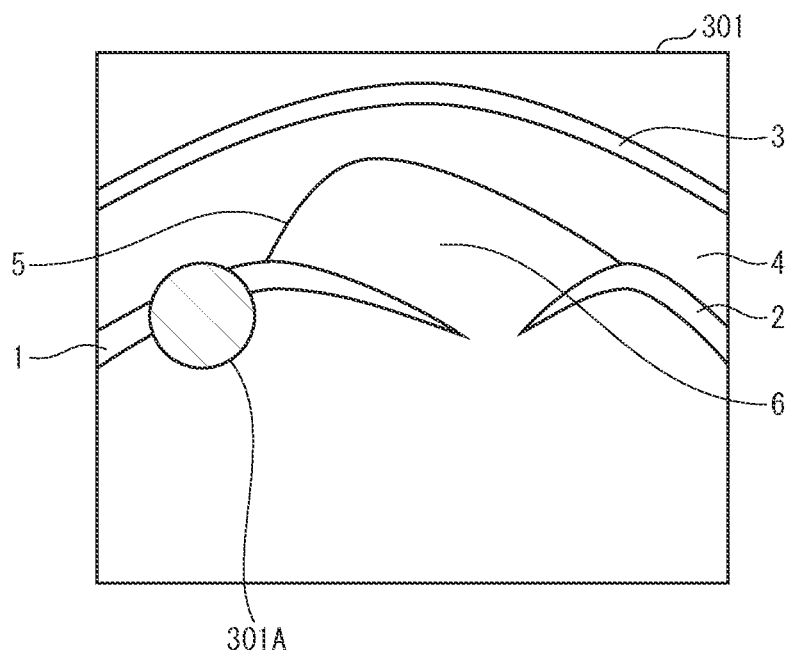

FIGS. 14A and 14B are schematic diagrams, each illustrating one example of a situation in which motion noise occurs in a B-mode image signal of a frame. In FIG. 14A, a Doppler signal detection region 301A is present over a large extent of the B-mode image 301. A Doppler signal is a signal that indicates current flow, but more fundamentally is a signal that captures movement. Therefore, when the operator moves the ultrasound probe 1001 by a large amount, the Doppler signal detection region 301A occupies a large extent of the B-mode image signal 301 as illustrated in FIG. 14A. Therefore, motion noise is assumed to have occurred when the Doppler signal detection region 301A occupies a large proportion of surface area of the B-mode image 301.

Next, in step S3003 the motion noise detector 3003 calculates a proportion of surface area of a high luminance region of the B-mode image signal of the frame which is occupied by the Doppler signal detection region. More specifically, with respect to a region of the B-mode image signal of the frame in which pixels have a predetermined luminance, the motion noise detector 3003 calculates a number of pixels in the region for which a Doppler signal appears as a fraction of a total number of pixels in the region. In the B-mode image, a high luminance region corresponds to a region in the subject in which hard tissue is present, and thus corresponds to bone or the like. Blood flow does not occur in such a region. Therefore, image noise is assumed to have occurred when, as illustrated in FIG. 14B, part of the Doppler signal detection region 301A is present in the image section 1 depicting bone, which in other words is a high luminance region of the B-mode image 301.

Next, in step S3004 the motion noise detector 3003 calculates an evaluation value for motion noise judgment and compares the evaluation value to a threshold value. An evaluation value p for motion noise judgment can be calculated as shown below in MATH. 1, wherein Mx represents an inter-frame luminance difference between B-mode image signals, My represents a proportion of surface area that a Doppler signal detection region occupies in the B-mode image signal of the frame, Mz represents a proportion of surface area that the Doppler signal detection region occupies in the high luminance region of the B-mode image of the frame, and ma, mb, and mc are constants.

$$p = ma \cdot Mx + mb \cdot My + mc \cdot Mz \qquad \text{[MATH. 1]}$$

Note that Mx, My, and Mz may each be normalized as values between 0 and 1 using a maximum value and a minimum value thereof. The higher the evaluation value p, the greater the probability that motion noise has occurred. When the evaluation value p for motion noise judgment is greater than or equal to the threshold value, the motion noise detector 3003 makes a judgment result of "motion noise present", and when the evaluation value p is less than the threshold value, the motion noise detector 3003 makes a judgment result of "motion noise not present".

(4) Process for Body Surface Pressure Detection

In step S1003 of FIG. 6, the pressure detector 3002 judges whether the ultrasound probe 1001 is not pressed against the body surface of the subject. If the ultrasound probe 1001 is pressed against the body surface of the subject when acquiring an ultrasound image, there is a possibility that an inflammation response does not appear in the ultrasound image due to pressure also being applied against blood vessels in the subject that are formed as result of angiogenesis. Therefore, an ultrasound image that is acquired while the ultrasound probe 1001 is pressed against the body surface of the subject is not an appropriate evaluation target image for rheumatoid arthritis and is therefore excluded from evaluation.

More specifically, the pressure detector 3002 performs the judgment in step S1003 based on whether an image section of the B-mode image signal that depicts an ultrasound gel layer between the body surface of the subject and the surface of the ultrasound probe 1001 satisfies a predetermined criterion.

Figure 15:
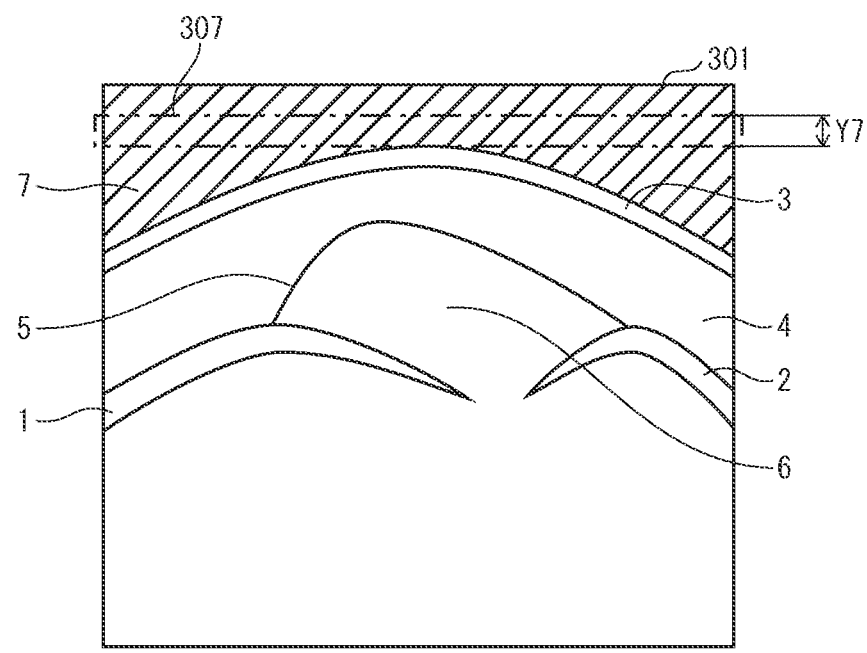
FIG. 15 relates to a process for body surface pressure detection.

FIG. 15 is provided to facilitate explanation of the process for body surface pressure detection. The pressure detector 3002 judges whether an image section 7 (section indicated by diagonal lines) depicting an ultrasound gel layer is present between the ultrasound probe 1001, positioned at the top edge of the B-mode image 301, and the image section 3 depicting the skin of the body surface of the subject. The image section 7 depicting the ultrasound gel layer has a low luminance and a low variance, and thus appears as a solid black section. Therefore, it is possible to determine whether the image section 7 depicting the ultrasound gel layer is present based on whether a section having a low luminance and a low variance is present close to the top edge of the B-mode image 301. In consideration of the above, as illustrated in FIG. 15, a gel judgment region 307, which is a rectangular region of predetermined range, is set close to the upper edge of the B-mode image 301, an average luminance and variance of pixels in the gel judgment area 307 is calculated, and the calculated values are compared to threshold values. The rectangular region located close to the top edge of the B-mode image 301, which is set as the gel judgment region 307, has a range Y7 which is preferably set as starting 3 mm to 5 mm from the top edge of the B-mode image 301. There is a possibility that a section at the top edge of the B-mode image 301 has non-zero luminance due to multiple reflection of ultrasound in the ultrasound probe 1001. The influence of the aforementioned multiple reflection can be avoided by ignoring a section of the B-mode image 301 which is within 3 mm of the top edge thereof, thereby ensuring accurate judgment of whether the image section 7 depicting the ultrasound gel layer is present.

Figure 16:
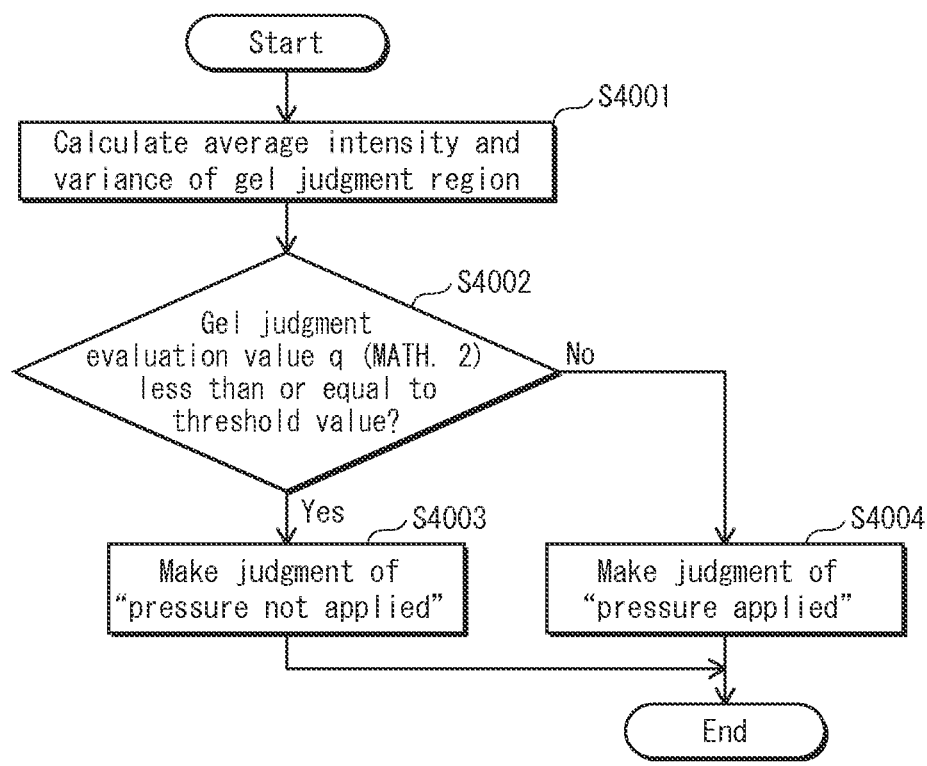
FIG. 16 is a flowchart illustrating the process for body surface pressure detection in the ultrasound diagnostic apparatus 1100.

FIG. 16 is a flowchart illustrating the process for body surface pressure detection.

In step S4001, the pressure detector 3002 calculates an average luminance and variance for the gel judgment region 307 in the B-mode image 301. The variance is used as an indicator of uniformity of a luminance distribution, which is a feature of the ultrasound gel layer.

Next, in step S4002 the pressure detector 3002 calculates an evaluation value for gel judgment and compares the evaluation value to a threshold value. An evaluation value q for gel judgment can be calculated as shown in MATH. 2, wherein Gx represents average luminance, Gy represents variance, and ga and gb are constants.

$$q = ga \cdot Gx + gb \cdot Gy \quad [\text{MATH. 2}]$$

The smaller the evaluation value q, the greater the probability that the ultrasound gel layer is present. When the evaluation value q for gel judgment is less than or equal to the threshold value, the pressure detector 3002 judges that a fixed ultrasound gel layer is present and thus makes a judgment result of "pressure not applied" (step S4003). On the other hand, when the evaluation value q is greater than the threshold value, the pressure detector 3002 judges that a fixed ultrasound gel layer is not present and thus makes a judgment result of "pressure applied" (step S4004). The pressure detector 3002 outputs the judgment result to the procedural technique judger 3004.

(5) Evaluation Target Determination

The procedural technique judger 3004 judges that the image of the corresponding frame has been acquired using appropriate procedural technique when a judgment result of step 1001 in FIG. 6 is "joint present", a judgment result of step S1002 is "motion noise not present", and a judgment result of step S1003 is "pressure not applied". In the above situation, the procedural technique judger 3004 outputs a judgment result indicating "perform quantification" to the shape quantifier 2003A and the inflammation quantifier 2003B. The procedural technique judger 3004 also outputs information indicating a position of the joint detection window 302 having a maximum evaluation value to the shape quantifier 2003A and the inflammation quantifier 2003B. On the other hand, the procedural technique judger 3004 judges that the image of the corresponding frame has not been acquired using appropriate procedural technique when a judgment result of step S1001 is "joint not present", a judgment result of step S1002 is "motion noise present", or a judgment result of step S1003 is "pressure applied". In the above situation, the procedural technique judger 3004 outputs a judgment result of "suspend quantification" to the shape quantifier 2003A and the inflammation quantifier 2003B, thereby completing processing with respect to the aforementioned frame.

Through the above configuration, the procedural technique judger 3004 accurately judges whether an ultrasound image signal of a frame has been acquired using appropriate procedural skill. Therefore, the above configuration enables more accurate determination of evaluation target frames to be used in disease progression score calculation.

(6) Swelling Score (GS) Calculation

Figure 17:
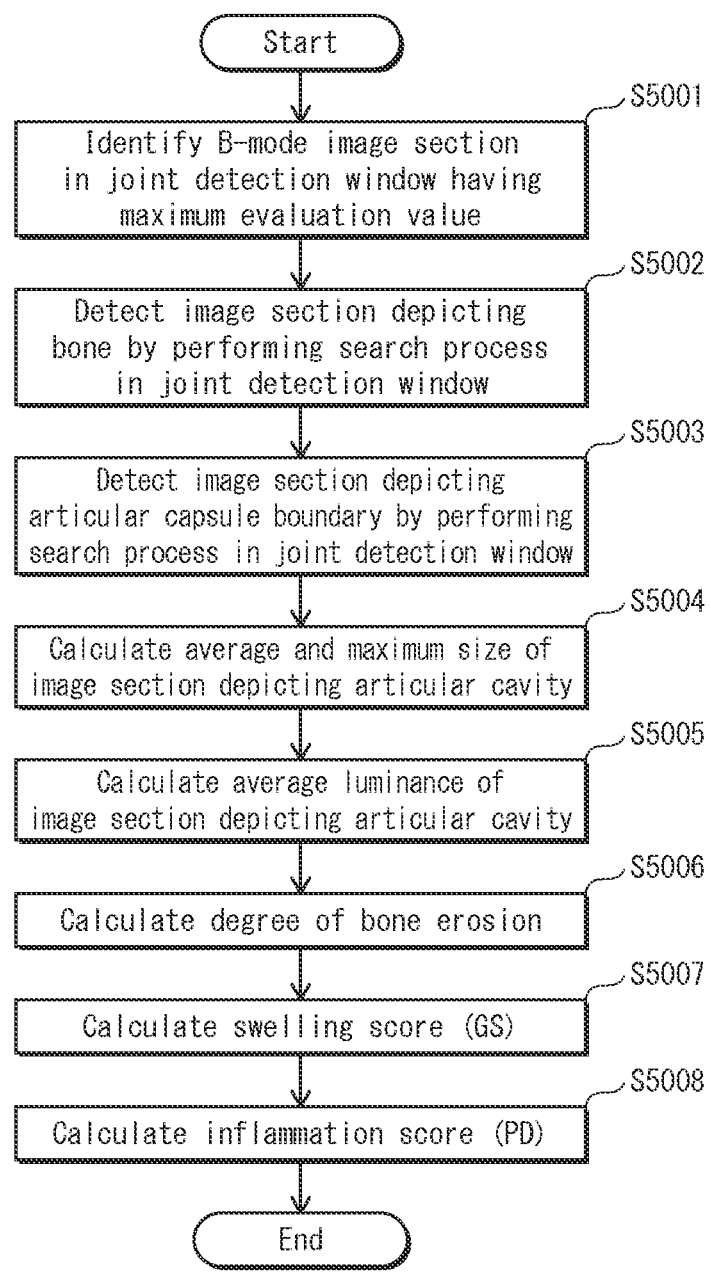
FIG. 17 is a flowchart illustrating a process for disease progression score calculation in the ultrasound diagnostic apparatus 1100.

In step S1004 of FIG. 6, the disease progression score calculator 2003 calculates disease progression scores. FIG. 17 is a flowchart illustrating the process for disease progression score calculation.

The shape quantifier 2003A calculates a disease progression score (swelling score) based on articular cavity size, luminance, and degree of bone erosion in a B-mode image.

(i) Calculation of Articular Cavity Size and Luminance

First, based on the information indicating the position of the joint detection window 302 having the maximum evaluation value, the shape quantifier 2003A identifies a section of the B-mode image 301 that depicts the joint (step S5001), and detects an image section depicting bone from a B-mode image section within the joint detection window 302 (step S5002).

Figure 18:
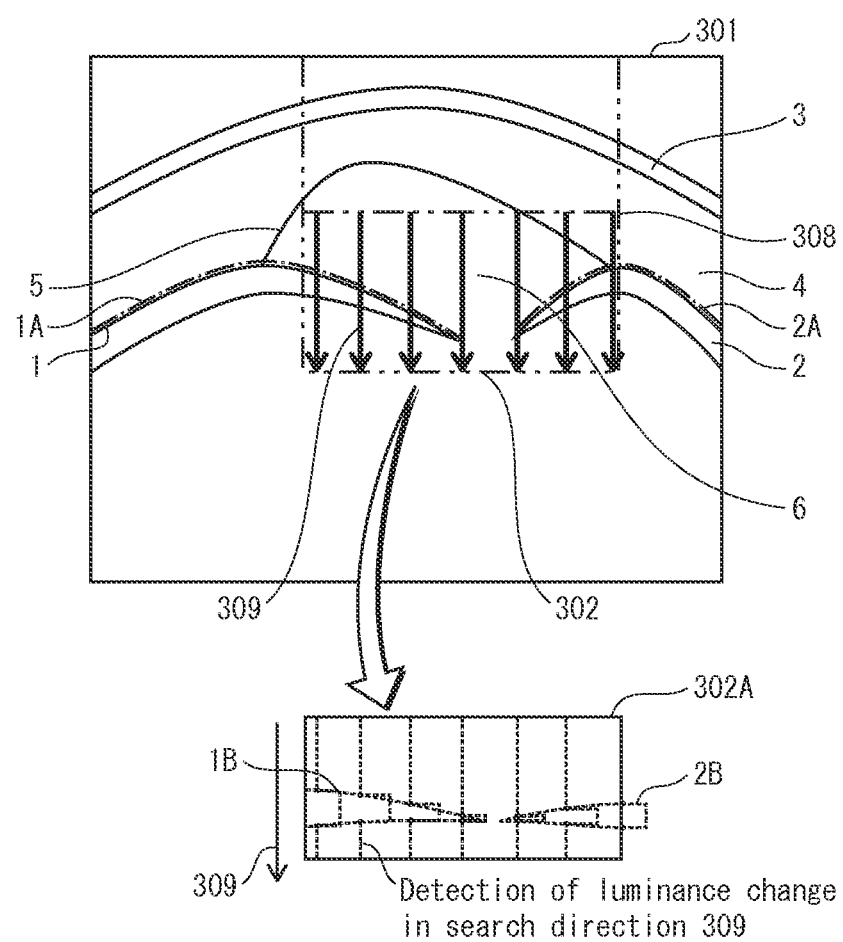
FIG. 18 is a schematic diagram relating to a process for detecting image sections 1 and 2 that depict bone.

FIG. 18 is a schematic diagram provided to facilitate explanation of a process for detecting the image sections 1 and 2 depicting bone. As explained further above, bone is a relatively hard tissue and is therefore rendered with a high luminance in an ultrasound image. The majority of incident ultrasound is reflected off a surface of bone. Therefore, only a section at the surface corresponding to bone cortex is rendered with a high luminance and an internal section of bone is not rendered.

The image sections 1 and 2 depicting bone are located lower in the joint detection window 302 than a vertical midpoint 308 of the joint detection window 302. Therefore, a B-mode image section included in a region 302A of the joint detection window 302 below the vertical midpoint 308 is defined as a search range. A downward direction starting from the vertical midpoint 308 of the joint detection window 302 is defined as a search direction 309 (direction indicated by arrows in FIG. 18), and luminance change in the search direction 309 is detected (step S5002). Probability of false boundary detections is reduced by performing the search process in a direction in which luminance changes from low luminance to high luminance. Due to the image sections 1 and 2 depicting bone having high luminance in the B-mode image 301, an active contour model (also referred to as snakes) or the like can be used to detect boundaries 1A and 2A between the image sections 1 and 2 depicting bone and other image sections surrounding the image sections 1 and 2. As illustrated in FIG. 18, during the above, when detected boundaries 1B and 2B, which are represented by rapid luminance change in the search direction 309, have a boundary position that changes smoothly in terms of a direction perpendicular to the search direction 309, the boundaries 1B and 2B can be respectively identified as the boundaries 1A and 2A of the image sections 1 and 2 depicting bone.

Next, the shape quantifier 2003A detects an image section depicting a boundary of the articular capsule.

Figure 19:
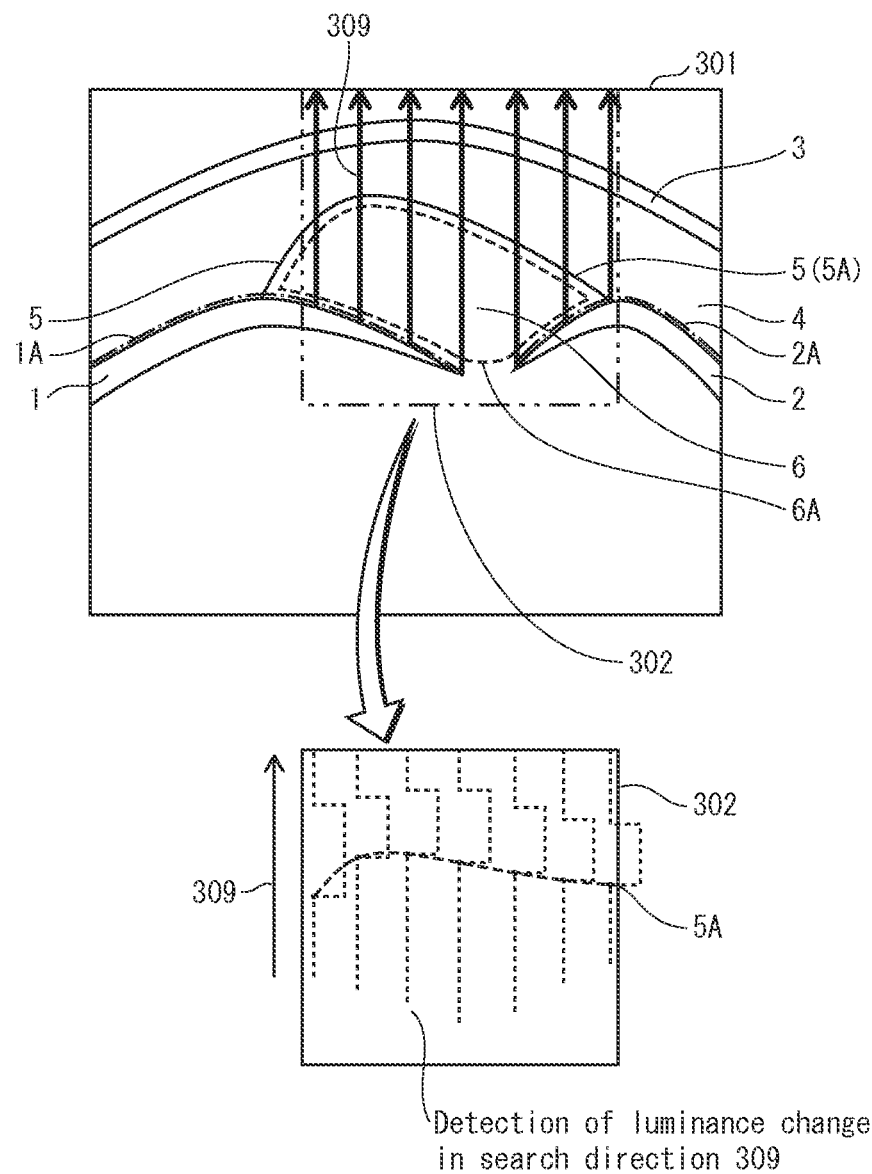
FIG. 19 is a schematic diagram relating to a process for detecting an image section 5 that depicts a boundary of an articular capsule.

FIG. 19 is a schematic diagram provided to facilitate explanation of a process for detecting the image section 5 depicting the boundary of the articular capsule. The image section 5 depicting the articular capsule is located above the image sections 1 and 2 depicting bone in the joint detection window 302. Therefore, a B-mode image section included in a region of the joint detection window 302 which is higher than the image sections 1 and 2 depicting bone is defined as a search range. Probability of false boundary detections is reduced, in the same way as described above, by performing the search process in a direction in which luminance changes from low luminance to high luminance. An upward direction starting from the boundaries 1A and 2A between the image sections 1 and 2 depicting bone in the joint detection window 302 and the surrounding image sections is set as a search direction 309 (direction indicated by arrows in FIG. 19), and luminance change in the search direction 309 is detected (step S5003). An image section of the B-mode image 301 that for example depicts a fatty layer and a muscle layer is located above the image section 5 depicting the articular capsule. The aforementioned image section has a greater luminance than the image section 6 depicting the articular cavity. Therefore, an active contour model or the like can also be used to detect a boundary 5A between the image section 5 depicting the articular capsule and the image section 6 depicting the articular cavity. As illustrated in FIG. 19, during the above, when the boundary 5A which is detected changes rapidly in the search direction 309, and when a boundary position in terms of the search direction 309 changes smoothly in a direction perpendicular to the search direction 309, the boundary 5A can be identified as the image section 5 depicting the articular capsule. The image section 5 may alternatively be identified by another image processing method such as a region expansion method based on degrees of similarity of luminance values.

Next, the shape quantifier 2003A calculates the size of the image section 6 depicting the articular cavity (step S5004). When the size of the image section 6 depicting the articular cavity is large, disease activity can be evaluated as being high. The size of the image section 6 depicting the articular cavity can for example be calculated by calculating distances in the vertical direction between the boundaries 1A and 2A of bone and the image section 5 (5A) depicting the articular capsule, or by calculating a surface area surrounded thereby. An average value and a maximum value are calculated for different positions along the direction perpendicular to the search direction 309.

Next, the shape quantifier 2003A calculates an average luminance of the image section 6 depicting the articular cavity (step S5005). When the average luminance of the image section 6 depicting the articular cavity is low, disease activity can be evaluated as being high. The average luminance of the image section 6 depicting the articular cavity can be calculated by calculating an average value of luminances of all pixels included in the image section 6, which is surrounded by the boundaries 1A and 2A of bone and the image section 5 (5A) depicting the articular capsule. The image section 6 depicting the articular cavity is a region surrounded by a peripheral edge 6A illustrated in FIG. 19. Note that the average luminance of the image section 6 depicting the articular cavity may alternatively be calculated as a median value of luminance in the image section 6 instead of a mean value of luminance.

(ii) Degree of Bone Erosion Calculation

Next, the shape quantifier 2003A calculates a degree of bone erosion 7 (step S5006). When the degree of bone erosion 7 is high, disease activity can be evaluated as being high.

Figure 20:
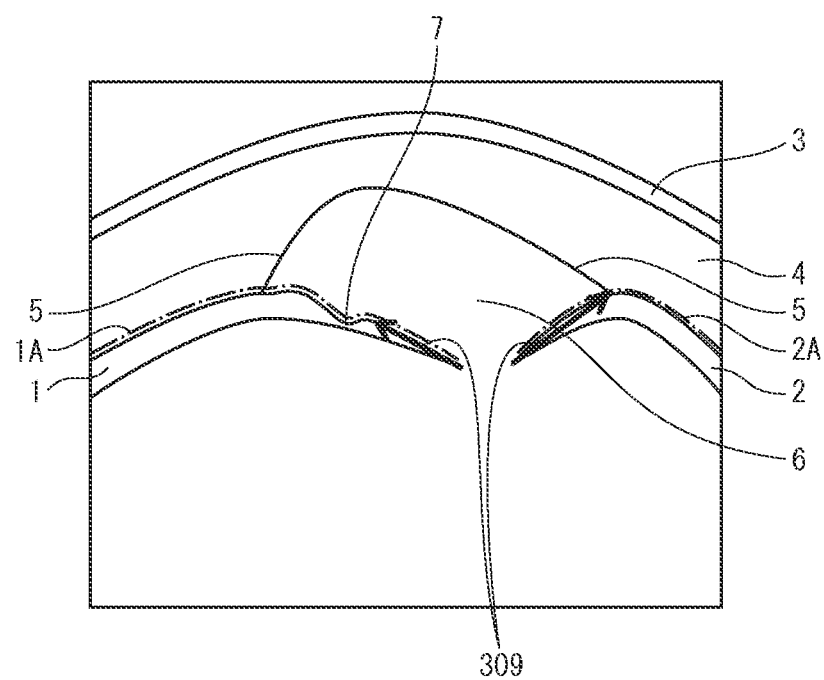
FIG. 20 is a schematic diagram relating to process for detecting a degree of bone erosion 7.

FIG. 20 is a schematic diagram relating to a process for detecting the degree of bone erosion 7. The degree of bone erosion 7 can be evaluated by evaluating smoothness of the boundaries 1A and 2A between the image sections 1 and 2 depicting bone and the image section 6 depicting the articular cavity. More specifically, as illustrated in FIG. 20, evaluation is performed through a search process in a search direction 309 from a lowermost part of the boundaries 1A and 1B. Note that the search direction 309 is toward the left from the lowermost part in the case of the boundary 1A and toward the right from the lowermost part in the case of the boundary 2A. Smoothness of each of the boundaries 1A and 1B is evaluated by calculating a function for the boundary through curve fitting and calculating errors relative to the function of the fitted curve.

Figure 21:
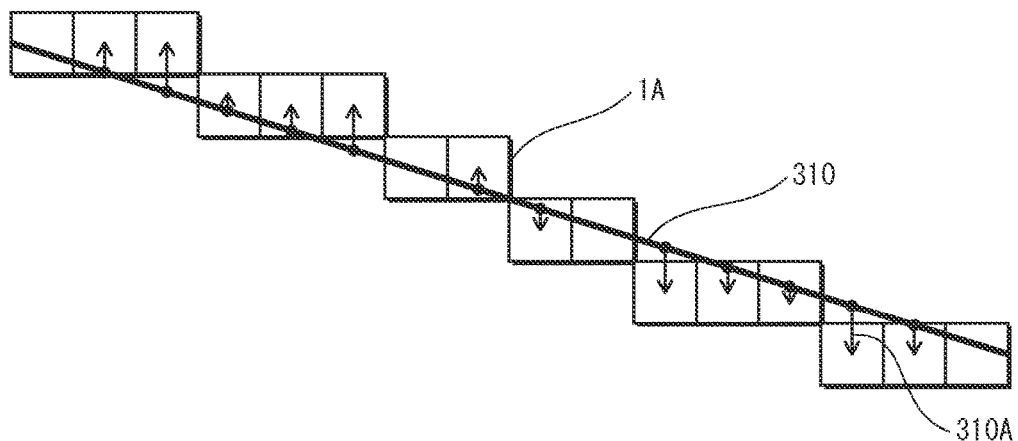
FIG. 21 is a schematic diagram illustrating one example of curve fitting with respect to a boundary of a healthy bone surface.
Figure 22:
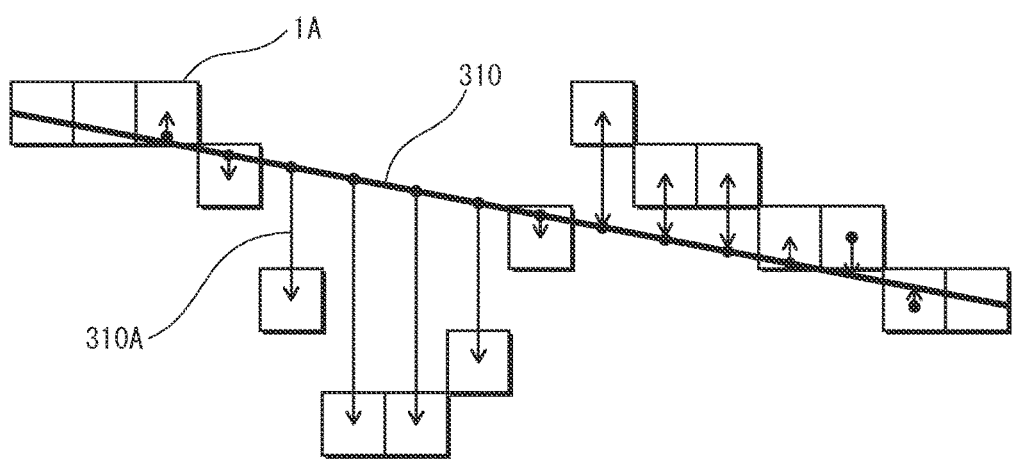
FIG. 22 is a schematic diagram illustrating one example of curve fitting with respect to a boundary of a bone surface exhibiting bone erosion.

FIG. 21 is a schematic diagram illustrating one example of curve fitting for a boundary of a healthy bone surface. FIG. 22 is a schematic diagram illustrating one example of curve fitting for a boundary of a bone surface exhibiting bone erosion. FIGS. 21 and 22 each illustrated one example of an image depicting a bone boundary 1A and a fitted curve 310 which has been fitted to the bone boundary 1A. Fitting errors 310A for the boundary of the eroded bone surface illustrated in FIG. 22 are large compared to the boundary of the healthy bone surface illustrated in FIG. 21. The degree of bone erosion can be evaluated by calculating a cumulative value of the fitting errors 310A along the fitted curve 310. Note that although the function used in curve fitting may be selected freely, preferably a degree of the function is selected such that the curve is not fitted to eroded sections of bone.

Furthermore, smoothness of a bone surface may alternatively be detected by calculating a first or second derivative of a bone boundary and detecting change in a direction along the bone surface. Through the above, the influence of variation in bone surface shape between individuals can be eliminated in evaluation bone surface smoothness.

(iii) Swelling Score Calculation

Next, the shape quantifier 2003A calculates a swelling score which is one type of disease progression score (S5007). The swelling score can be calculated according to MATH. 3, wherein GSx represents size of the image section 6 depicting the articular cavity, GSy represents luminance of the image section 6, GSz represents the degree of bone erosion, and gsa, gsb, and gsc are constants.

$$GS = gsa \cdot GSx + gsb \cdot GSy + gsc \cdot GSz \quad \text{[MATH. 3]}$$

Thorough investigation by the inventors has shown that disease activity can be accurately evaluated using the swelling score (GS), which is a linear combination of three parameters GSx, GSy, and GSz that have a strong relationship to disease activity of rheumatoid arthritis. Note that GSx, GSy, and GSz may each be normalized as a value between 0 and 1 using a maximum value and a minimum value thereof. As explained further above, the shape quantifier 2003A outputs the swelling score to the memory 1005 and the memory 1005 stores the swelling score therein (step S1004). The shape quantifier 2003A also outputs information indicating position of the image section 6 depicting the articular cavity to the inflammation quantifier 2003B.

Through the above configuration, objectivity of evaluation is improved by calculating, for each evaluation target frame, a disease progression score quantifying disease activity, using a signal of a target image section included in a B-mode image signal of the evaluation target frame.

(7) Inflammation Score (PD) Calculation

In step S5008 of FIG. 17, the inflammation quantifier 2003B receives the information indicating position of the image section 6 depicting the articular cavity as input and calculates an inflammation score, which is one type of disease progression score, based on the Doppler mode image signal.

Based on extent of the image section 6 depicting the articular cavity, which is identified by the shape quantifier 2003A in step S5005, the inflammation quantifier 2003B sets the image section 6 as a region of interest (ROI). The inflammation quantifier 2003A calculates a surface area (PDy) of the ROI. The inflammation quantifier 2003B also calculates a surface area (PDx) occupied by pixels for which a Doppler signal is detected among all pixels included in the image section 6 depicting the articular cavity, which constitutes the ROI. A judgment of whether a Doppler signal is detected for a given pixel can be performed as appropriate based on whether a Doppler signal that exceeds a predetermined threshold value is detected for the pixel. The inflammation score can be calculated according to MATH. 4 as the quotient of the surface area (PDx) divided by the surface area (PDy).

$$PD = PDx/PDy \quad \text{[MATH. 4]}$$

During the above, alternatively the ROI may be set as a region that includes at least one part of the image section 6 depicting the articular cavity, and the surface area (PDy) of the ROI and the surface area (PDx) occupied by Doppler signals in the ROI may be calculated with respect to the alternative ROI. The one part of the image section 6 may for example be a rectangular image section of fixed size that is set based on results of bone detection. In such a configuration, the surface area (PDy) has a fixed value.

Thorough investigation by the inventors has shown that disease activity can be evaluated accurately and effectively using the swelling score (PD), which is calculated based on whether Doppler signals are detected for pixels. As explained further above, the inflammation quantifier 2003B outputs the inflammation score to the memory 1005 and the memory 1005 stores the inflammation score therein (step S1004).

Through the above configuration, objectivity of evaluation is improved by calculating, for each evaluation target frame, a disease progression score quantifying disease activity, using a signal of a target image section included in a B-mode image signal and a Doppler mode image signal of the evaluation target frame.

(8) Disease Progression Score Selection, Display, and Storage

As explained further above, in step S1005 of FIG. 6 the selector 2004 receives the disease progression scores (swelling scores and inflammation scores) stored in the memory 1005 as input, and selects at least one most suitable disease progression score from among the inputted swelling scores and at least one most suitable disease progression score from among the inputted inflammation scores, in accordance with a predetermined numerical process. In the present embodiment, the selector 2004 selects a maximum value among disease progression scores stored in the memory 1005 as the most suitable disease progression score.

However, alternatively the selector 2004 may select, as the most appropriate disease progression score, a mean value of the disease progression scores which indicates an average disease activity or a median value of the disease progression scores which indicates an intermediate disease activity. Further alternatively, the disease progression score which is selected may be a disease progression score that is identical or closest to at least one of the maximum value, the mean value, and the median value of the plurality of disease progression scores. Through the above, a selection criterion for selecting a most suitable disease progression score in accordance with a predetermined numerical process may be set as appropriate based on conditions such as state of a disease, characteristics of a subject, and examination guidelines of a doctor or hospital.

Note that examination may alternatively be performed by selecting most suitable disease progression scores using a plurality of selection criteria that are each in accordance with a predetermined numerical process. Through the above, examination can be performed by selecting selection criteria based on each of various conditions such as state of a disease and characteristics of a subject. In such a situation, selection criteria that are used in selection of disease progression scores during examination should preferably be output to the memory 1005 and stored therein.

Also, as explained further above, each most suitable disease progression score selected in the accordance with the predetermined numerical process is also output to the memory 1005 and stored therein. At the same time, the numerical process which is used in disease progression score selection, or the selection criterion in accordance therewith, may be output to the memory 1005 and stored therein. Through the above configuration, disease progression scores can be selected using a same selection criterion as has been used in selection of previously calculated disease progression scores. As a consequence, it is easier to compare new evaluation results with previous evaluation results when monitoring disease progression over time, for example through periodic examinations.

Note that in a situation in which a disease progression score is corrected, the operation console 1009 acquires correction information from the operator and stores the correction information in the memory 1005. When the correction is with respect to the articular capsule or a Doppler signal, the shape quantifier 2003A and the inflammation quantifier 2003B recalculate the disease progression scores based on the correction information.

2. Display Screen Relating to Ultrasound Diagnostic Apparatus 1100

(1) Operation Screen

The following explains an operation screen for the ultrasound diagnostic apparatus 1100.

An image displayed on a display screen of the display 1008 is explained below assuming a configuration in which input to the ultrasound diagnostic apparatus 1100 is performed through a touch operation on the operation console 1009, which is a touch panel disposed on the screen of the display 1008.

Figure 23:
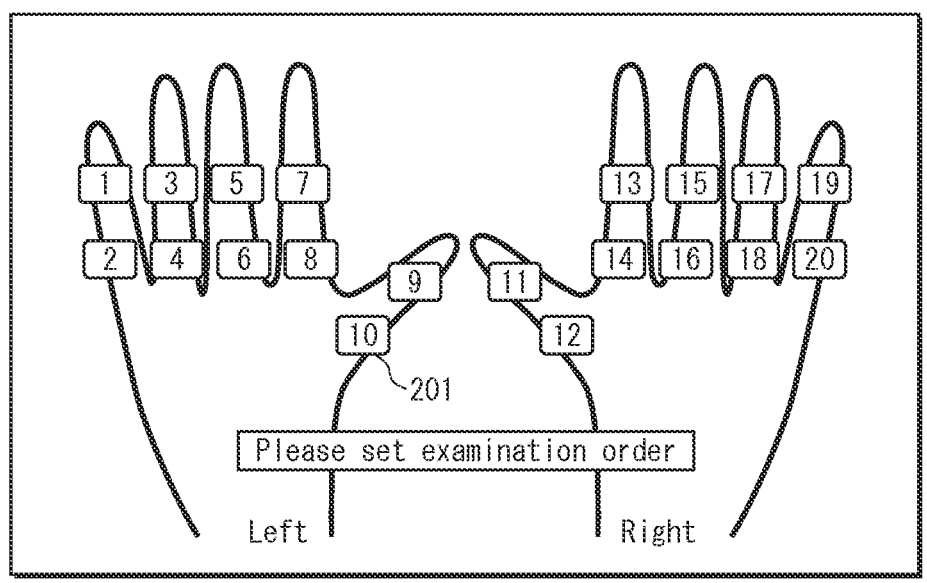
FIG. 23 illustrates an operation input screen for registering an examination order.

Prior to commencing examination, the operator registers an examination order for the finger joints. FIG. 23 illustrates an operation input screen of the ultrasound diagnostic apparatus 1100 for registering the examination order. An order in which icons 201, indicating positions of joints, are touched is registered as the examination order for the indicated joints. Numbers indicating the examination order are displayed in the icons 201. When the operator wishes to change an initially set examination order indicated by numbers displayed in the icons 201, further touching of the icons 201 updates a registered examination order to match an order in which the touching is performed.

The following explains an operation screen for the ultrasound diagnostic apparatus 1100 during examination of a single finger joint.

Figure 24:
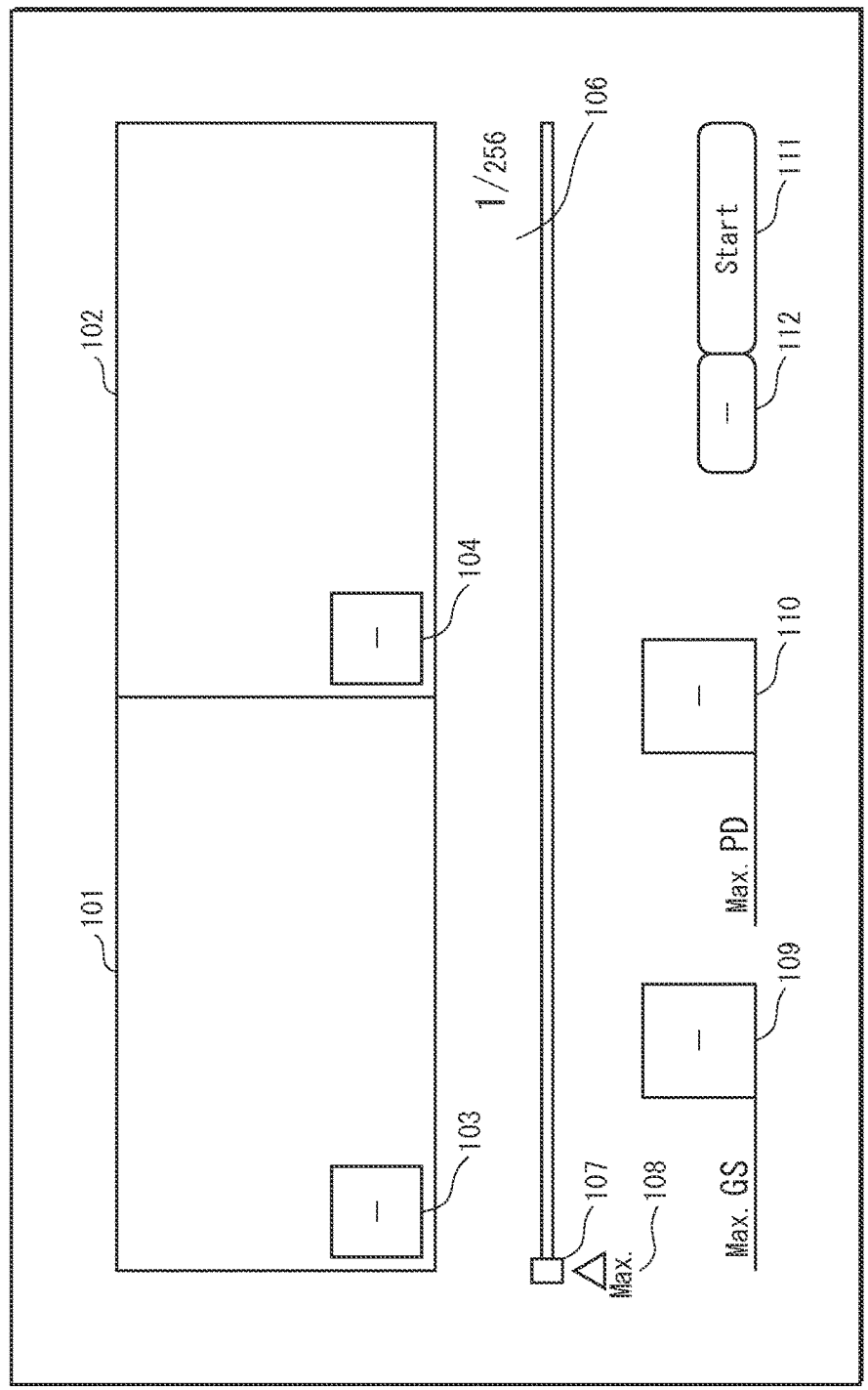
FIG. 24 illustrates a display screen prior to measurement.

FIG. 24 illustrates a display screen prior to measurement. As illustrated in FIG. 24, the display screen includes a B-mode image display area 101, a Doppler mode image display area 102, a swelling score display area 103, an inflammation score display area 104, and a frame number 106. The display screen also includes a slider 107 that indicates a frame position, a selected swelling score display area 109 indicating, for example, a maximum value of swelling scores calculated during examination, a selected inflammation score display area 110 indicating, for example, a maximum value of inflammation scores calculated during examination, a button 111 for starting or stopping measurement, and a next button 112 for confirming a disease progression score and proceeding to examination of a next finger joint.

Figure 25:
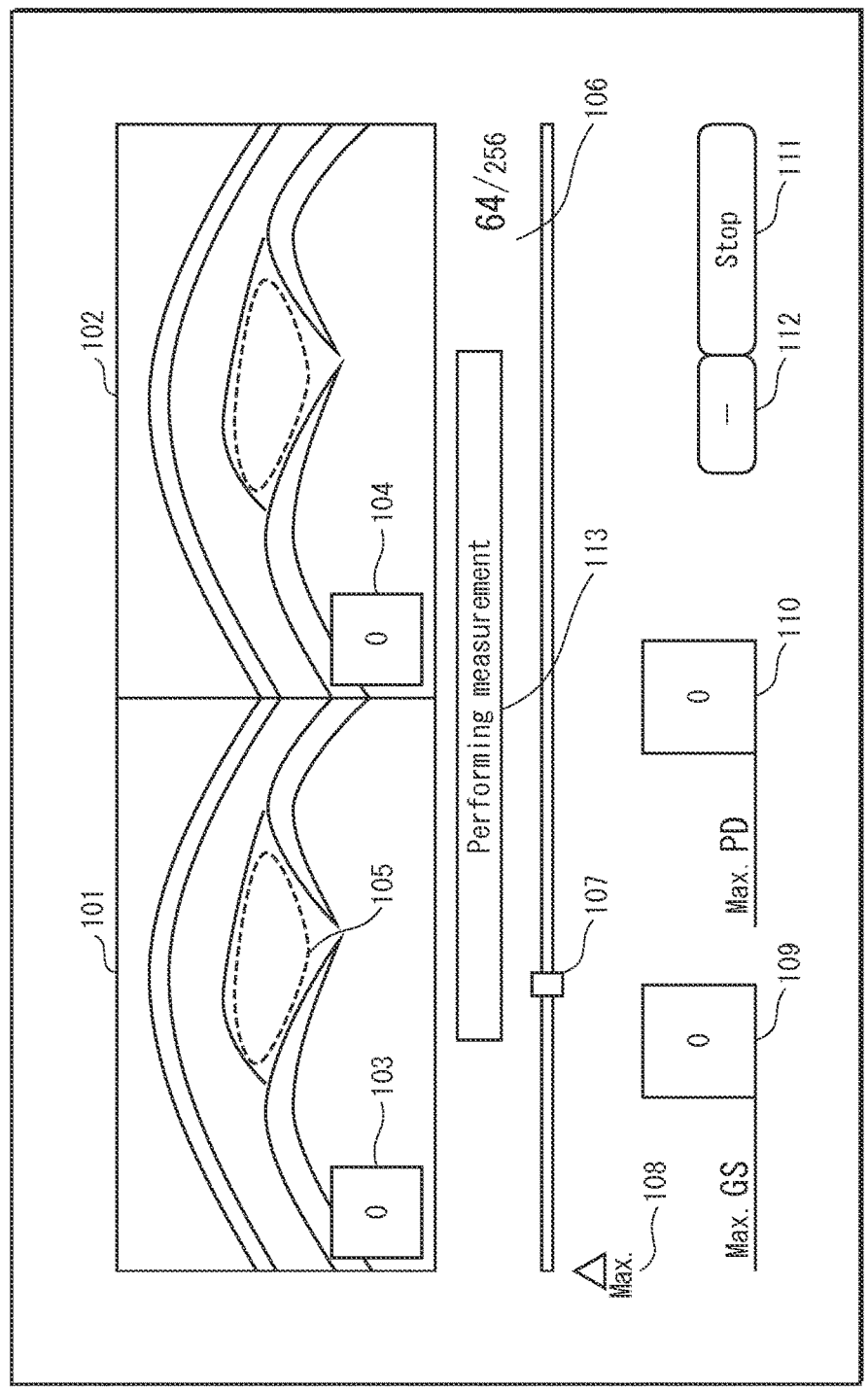
FIG. 25 illustrates a display screen during measurement.

When the display screen described above is displayed, upon the operator touching the button 111, measurement in step S1001 of FIG. 6 is started and, as illustrated in FIG. 25, display changes to a display screen for display during measurement which includes a message 113. An acquired B-mode image is displayed in the B-mode image display area 101 in real-time and an acquired Doppler mode image is displayed in the Doppler mode image display area 102 in real-time. A boundary 105 of an articular capsule which is detected by the ultrasound diagnostic apparatus 1100 is superimposed on both the B-mode image and the Doppler mode image.

Figure 26:
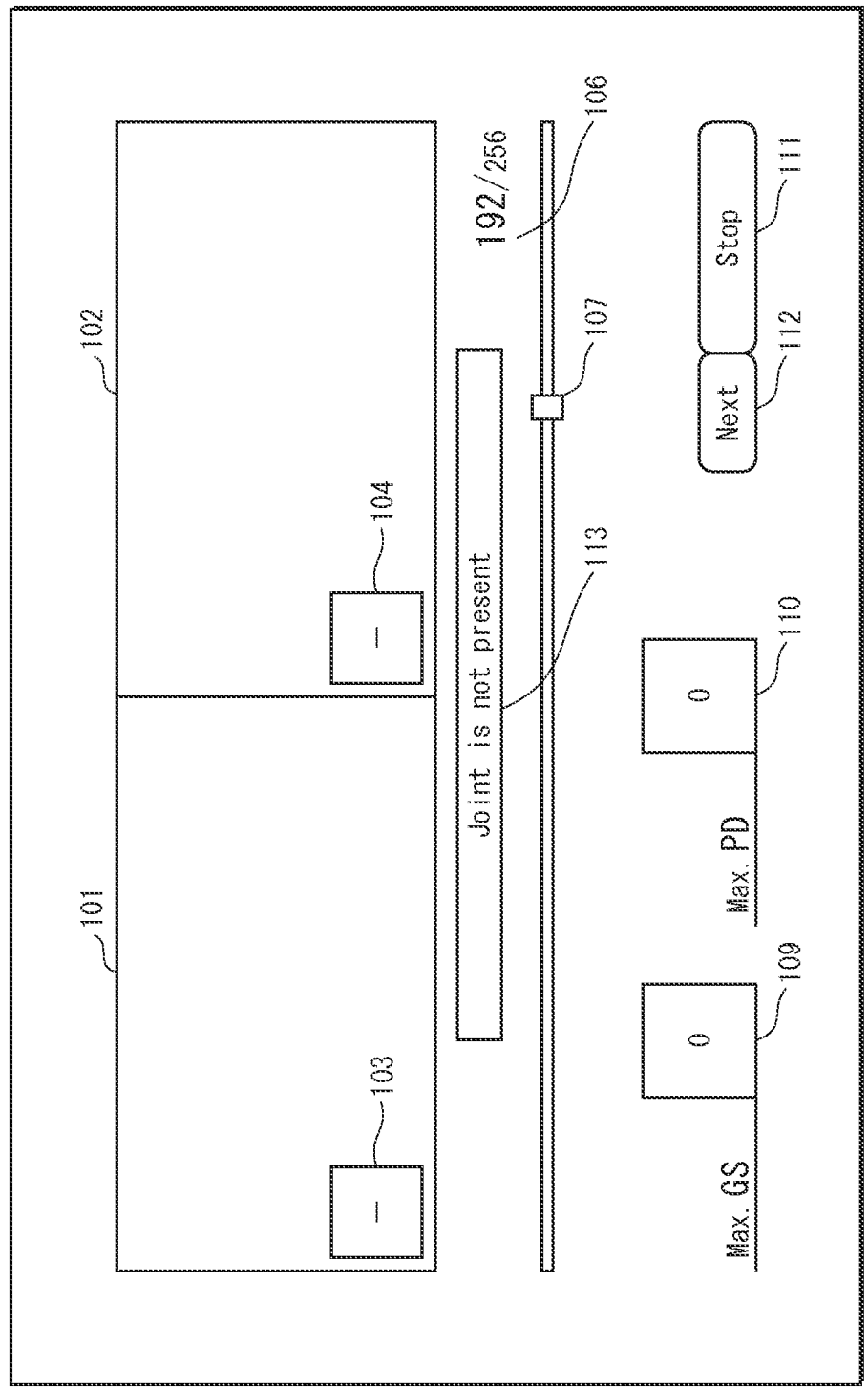
FIG. 26 illustrates a display screen displaying a warning message indication that a joint is not present in an image.
Figure 27:
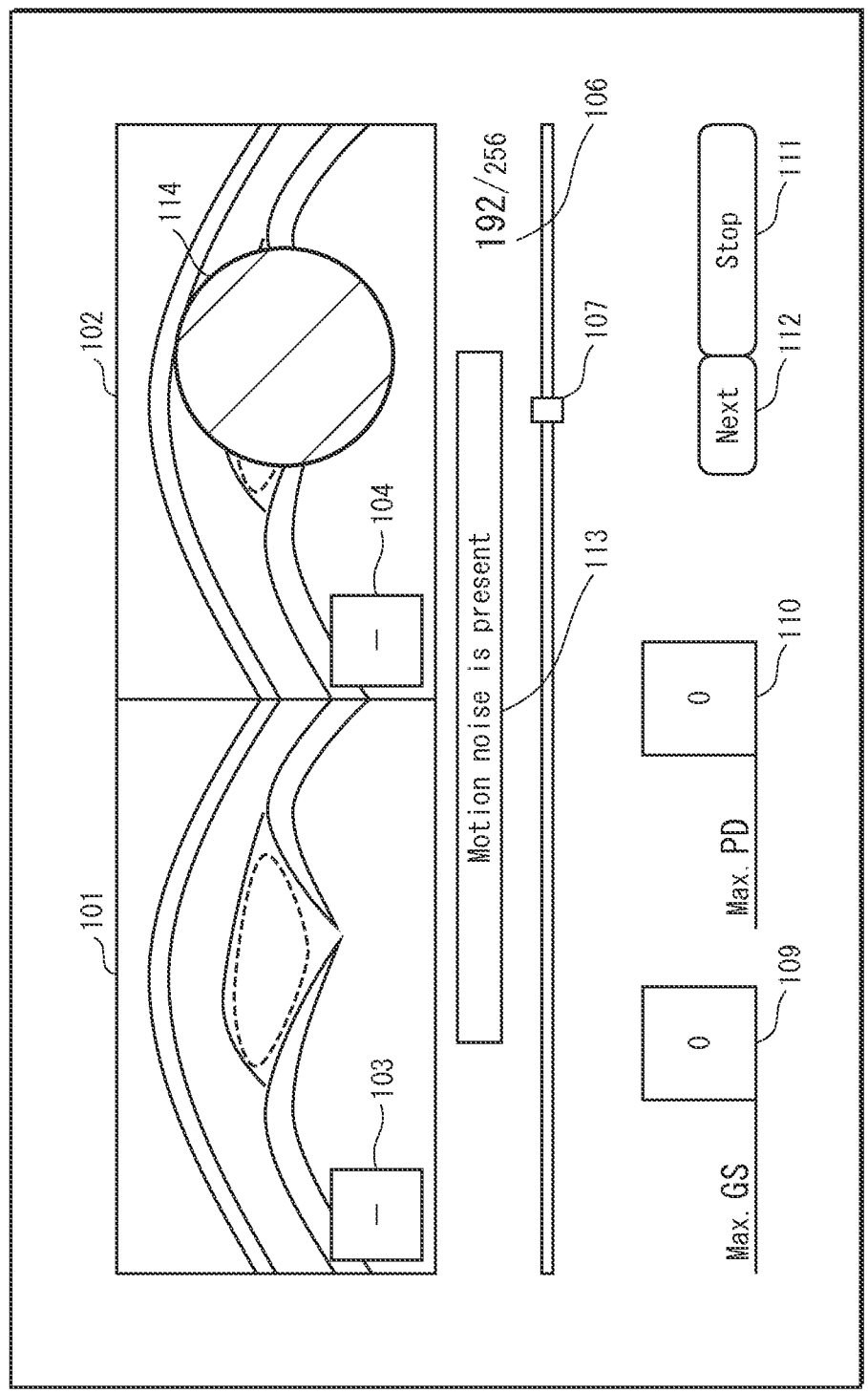
FIG. 27 illustrates a display screen displaying a warning message indicating that a Doppler mode image is caused by motion noise.
Figure 28:
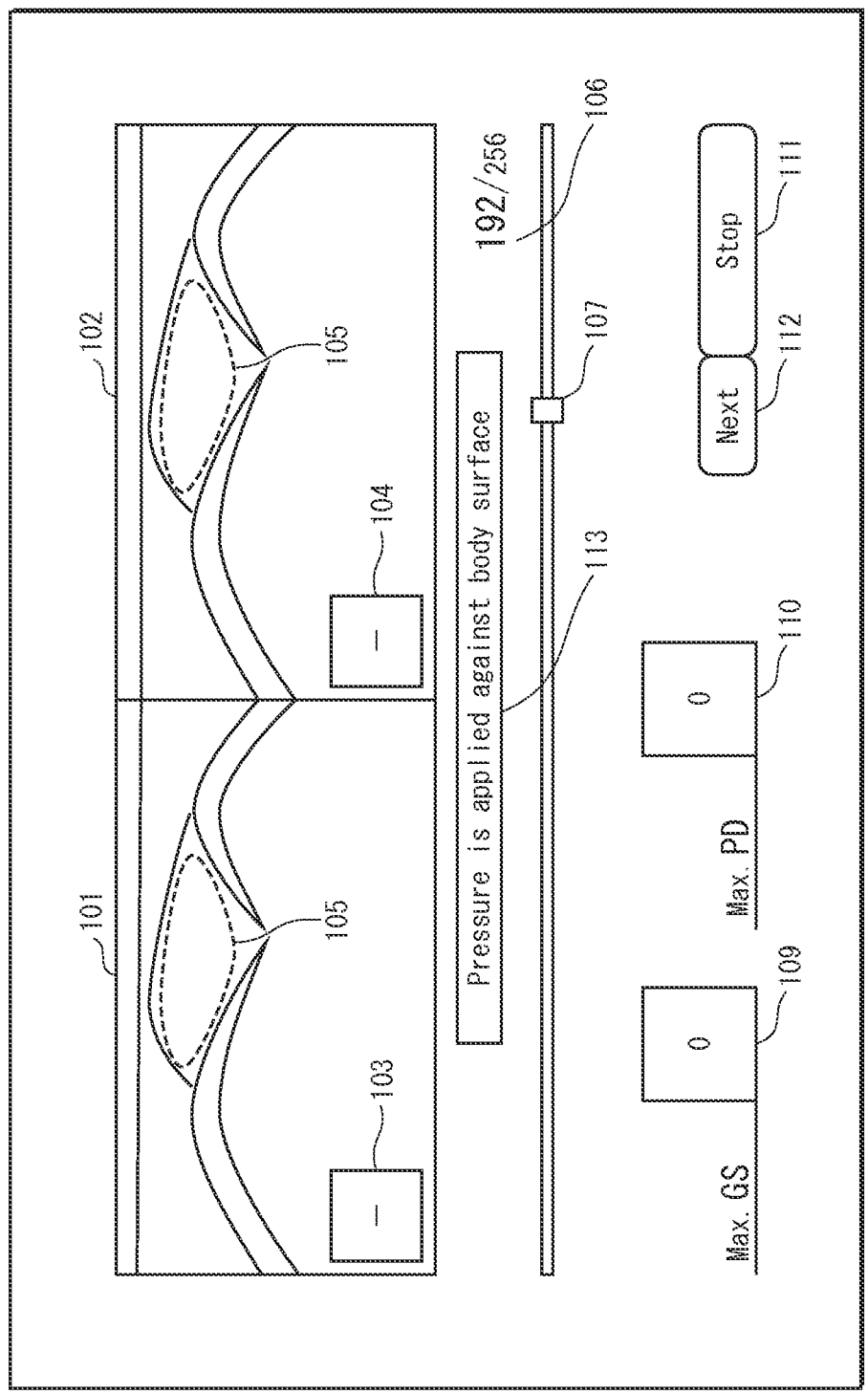
FIG. 28 illustrates a display screen displaying a warning message indicating that an ultrasound probe is applying pressure against a body surface of a subject.

When a joint is judged to not be present in image in step S1001, the message 113 is displayed as a warning that the joint is not present in the image, as illustrated in FIG. 26. When a Doppler mode image is judged to be caused by motion noise in step S1002, the message 113 is displayed as a warning, as illustrated in FIG. 27, without calculating a disease progression score. When the ultrasound probe 1001 is judged to be applying pressure against the body surface of the subject in step S1003, disease progression scores are not calculated and the message 113 is displayed as a warning as illustrated in FIG. 28.

Figure 29:
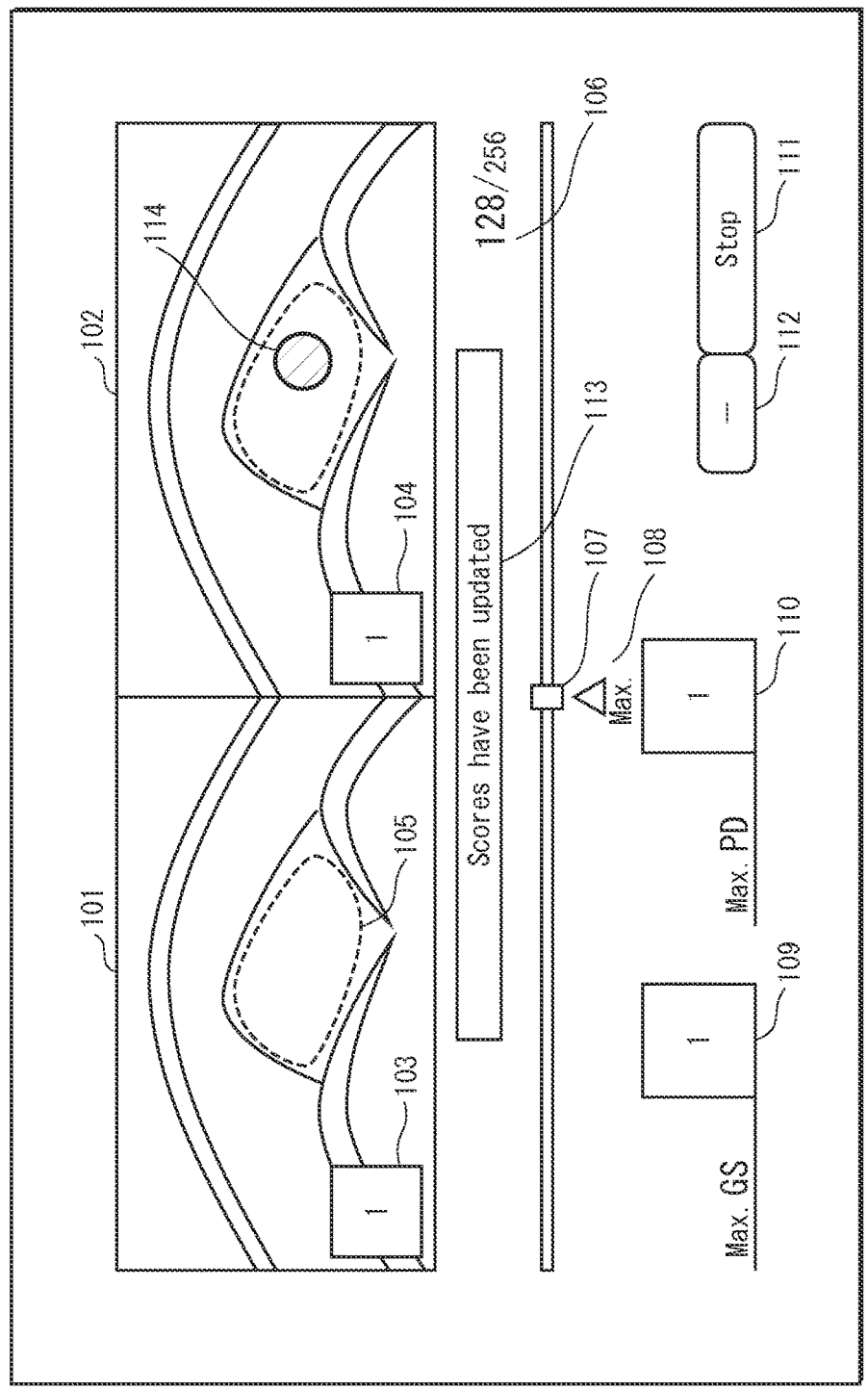
FIG. 29 illustrates a display screen displaying disease progression scores that have been measured.

When a cross-section of the finger joint in which disease progression has occurred is captured through movement of the ultrasound probe 1001 by the operator, a display screen including measured disease progression scores is displayed as illustrated in FIG. 29. More specifically, a Doppler signal region 114 indicating a region in which blood flow occurs is displayed on the Doppler mode image, and a maximum swelling score and a maximum inflammation score, which are examples of most suitable disease progression scores, are updated. An icon 108 is also displayed for each of the maximum disease progression scores (maximum swelling score and maximum inflammation score), indicating a frame for which the aforementioned maximum disease progression score is calculated. When a swelling score and an inflammation score are calculated in step S1004, the swelling score is displayed in the swelling score display area 103 and the inflammation score is displayed in the inflammation score display area 104. When maximum values of the aforementioned disease progression scores, which are examples of most suitable disease progression scores, are selected in step S1005, the maximum swelling score is displayed in the selected swelling score display area 109 and the maximum inflammation score is displayed in the selected inflammation score display area 110.

Figure 30:
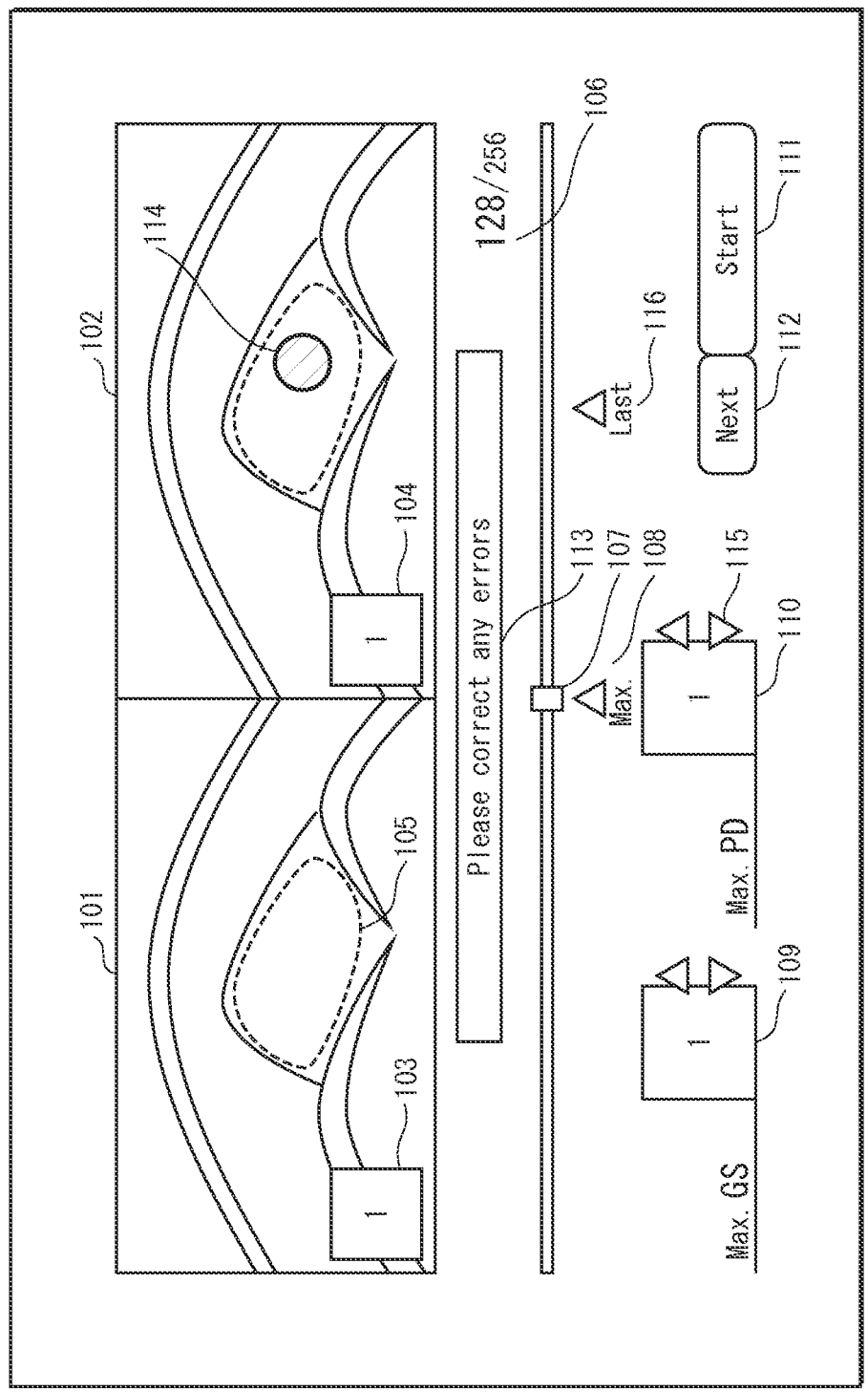
FIG. 30 illustrates a display screen indicating that measurement is complete.

When the display screen described above is displayed, upon the operator touching the button 111 for starting or stopping measurement, a display screen indicating that measurement is complete is displayed as illustrated in FIG. 30. Through step S1006, a maximum disease progression score among swelling scores, a maximum disease progression score among inflammation scores, ultrasound images of frames for which the maximum disease progression scores were calculated, and an icon 116 indicating a last frame to be examined are displayed.

When the operator touches the icon 116 indicating the last frame, the ultrasound image of the last frame is displayed. Through the above, when the ultrasound diagnostic apparatus acquires a new frame during examination which the operator considers to be inappropriate and selects the frame as an evaluation target frame, the operator can manually change frames which are used for evaluation. A button 115 for disease progression score correction is also displayed. When an appropriate disease progression score is not obtained, the operator can correct measurement results by pressing the button 115 for disease progression score correction. Furthermore, when the Doppler signal region 114 does not correspond to blood flow arising due to inflammation and instead corresponds to a blood vessel, the operator can delete the Doppler signal region 114. When no correction is necessary, the operator can proceed to measurement of a next finger joint by pressing the next button 112.

Figure 31:
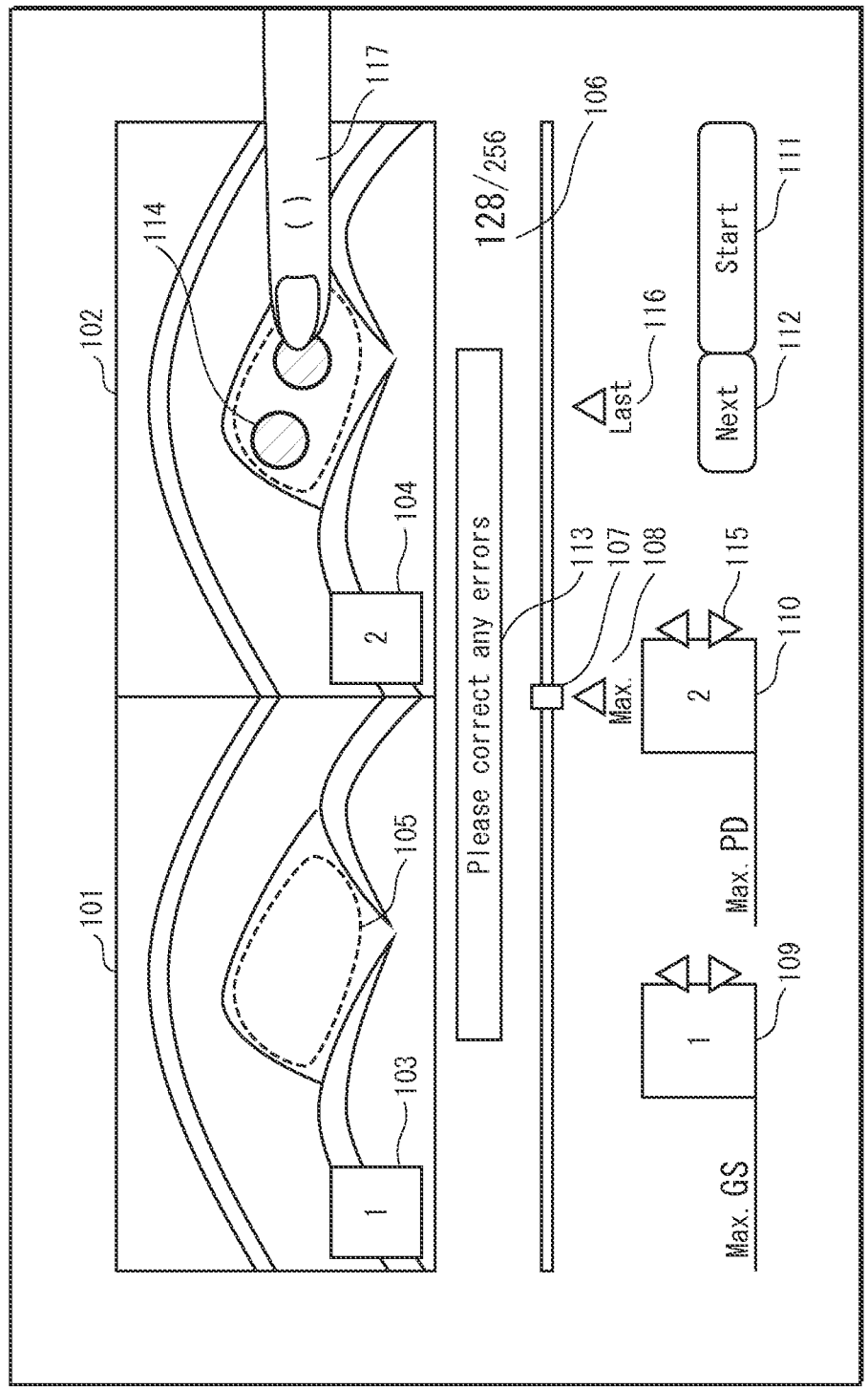
FIG. 31 illustrates a display screen during a correction operation.
Figure 32:
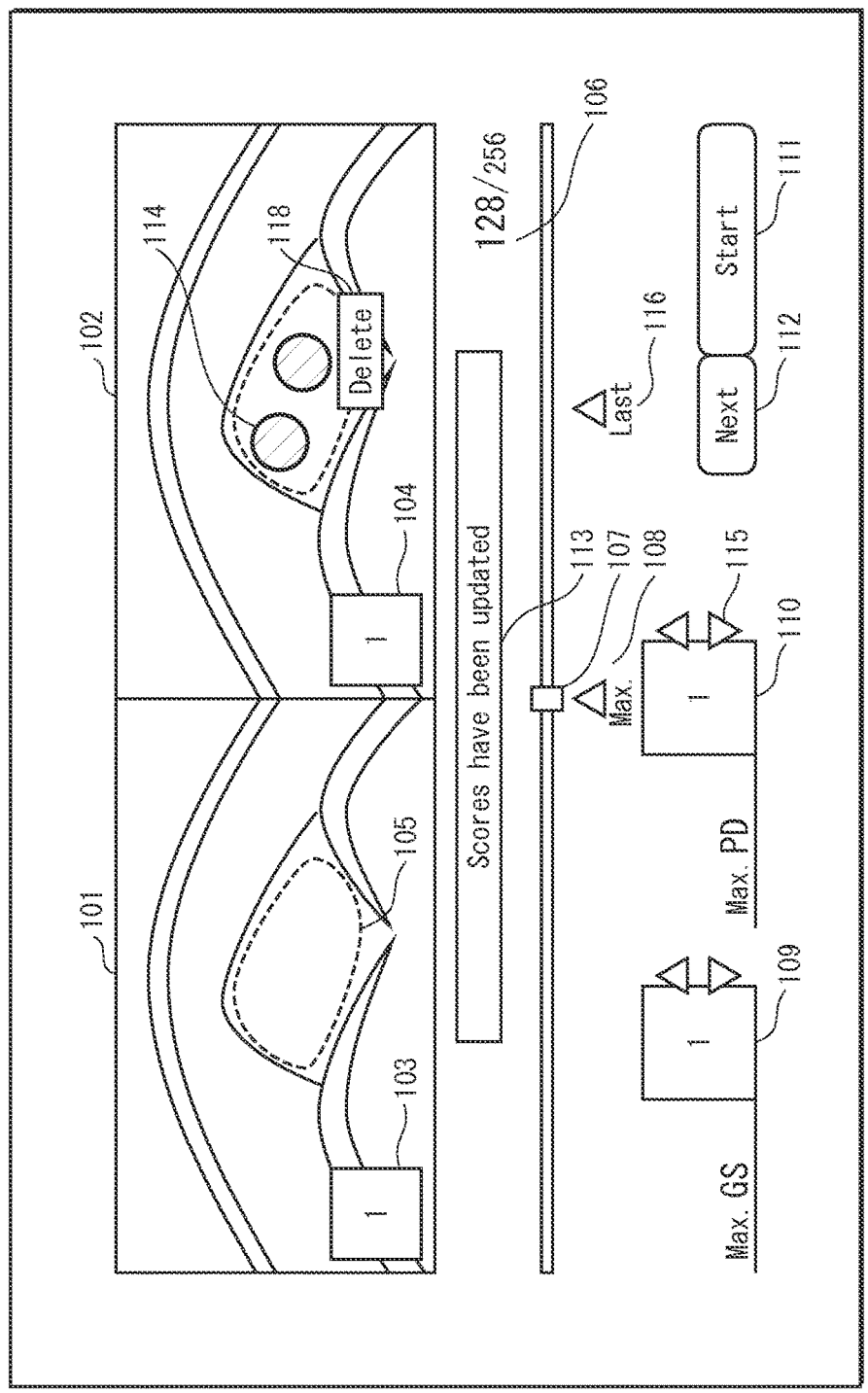
FIG. 32 illustrates a display screen after the correction operation.

FIG. 31 illustrates a display screen during a correction operation. During the correction operation, the operator can select the Doppler signal region 114 for deletion by touching the Doppler signal region 114 using a finger 117. Through the above operation, as illustrated in FIG. 32, the Doppler signal region 114 is deleted from the Doppler mode image, an icon 118 indicating deletion is displayed, and the disease progression scores are updated in accordance with the deletion. Although not illustrated in the drawings, the boundary 105 of the articular capsule can be corrected using the same method and the disease progression scores are updated in accordance with the correction.

In step S1007, once evaluation of all ultrasound images has been completed for the finger joint, examination is completed through an operation by the operator and the display screen for measurement completion is displayed as illustrated in FIG. 30. Alternatively, the display screen illustrated in FIG. 30 may be continuous displayed. When a new examination is to be performed for the same finger joint, the process is repeated from step S1001 and the display screen illustrated in FIG. 25 is displayed.

(2) Examination Results Display Screen

Figure 33:
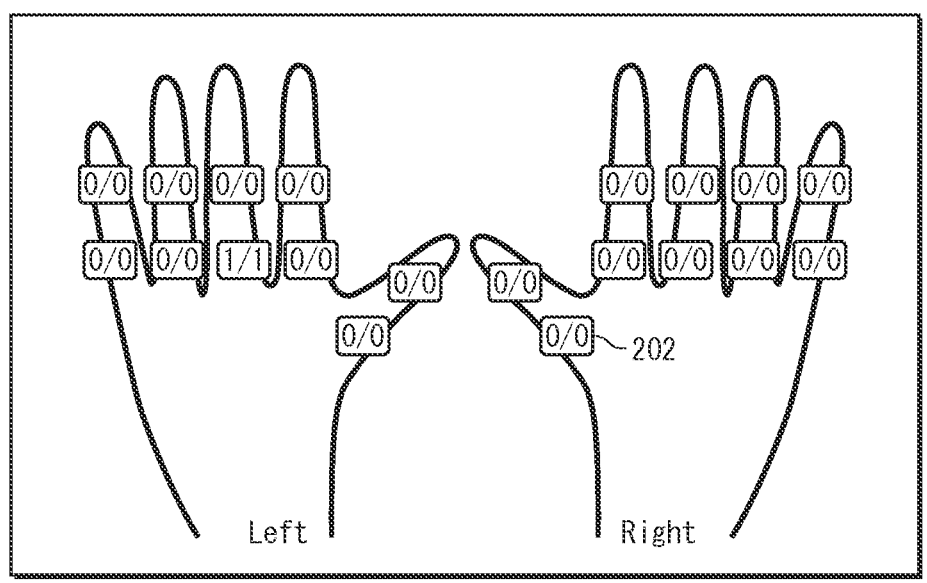
FIG. 33 illustrates a display screen displaying examination results for each finger joint.

Once all ultrasound images have been evaluated for all of the finger joints, examination results are displayed. FIG. 33 illustrates a display screen indicating examination results for each of the finger joints. The display screen illustrated in FIG. 33 may be displayed once examination has been completed for all of the finger joints, or alternatively may be displayed each time the next button 112 is touched.

In FIG. 33, an icon 202 indicating disease progression scores is displayed for each of the finger joints. A number on the left-hand side of the icon 202 indicates a swelling score for the finger joint and a number on the right-hand side of the icon 202 indicates an inflammation score for the finger joint. Display of the icon 202 indicating the disease progression scores may be emphasized for a finger joint having high disease progression scores, for example by displaying the icon 202 as a certain color.

When the operator touches one of the icons 202 indicating disease progression scores for a corresponding finger joint, the display screen for measurement completion (FIG. 30), which includes disease progression scores for the finger joint and an ultrasound image of a frame for which a most suitable disease progression score is calculated for the finger joint, is displayed.

Figure 34:
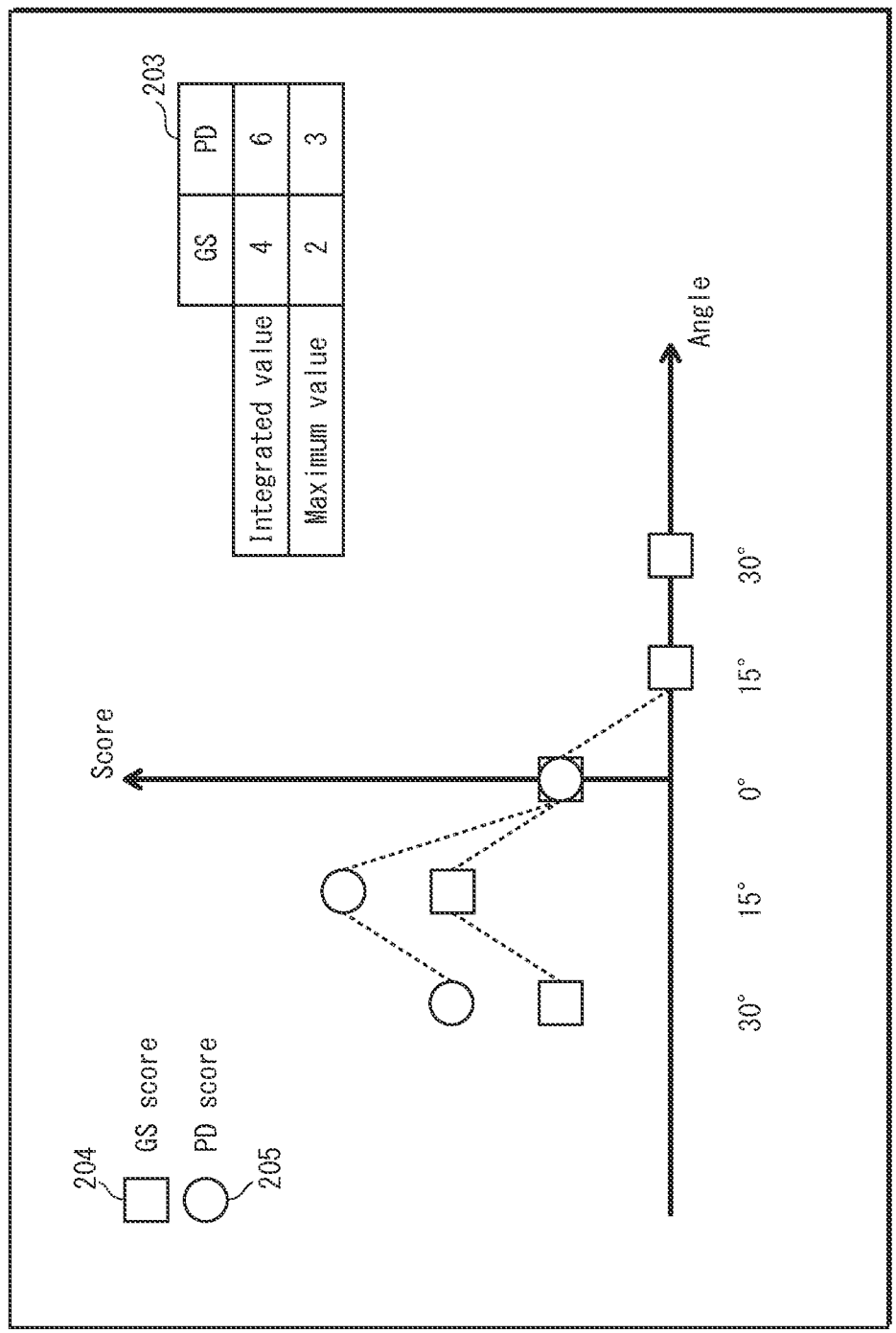
FIG. 34 illustrates a display screen displaying examination results that indicate disease progression scores calculated for one finger joint from ultrasound image signals of a plurality of frames.

When the operator performs a long touch operation on one of the icons 202 indicating the disease progression scores for a corresponding finger joint, as illustrated in FIG. 34, examination results for the finger joint are displayed as a graph of disease progression scores calculated from ultrasound images of a plurality of frames with respect to the same finger joint. FIG. 34 illustrates one example of a display method in which disease progression scores are displayed for each different inclination angle of the ultrasound probe 1001. In FIG. 34, a swelling score 204 and an inflammation score 205 are displayed for each angle. Also, a maximum value and an integrated value for all of the angles are displayed for each of the aforementioned types of disease progression score as indicated by reference sign 203. By keeping a record of the disease progression scores for each angle as described above, when disease progression is observed over time, for example through periodic examinations, it is easy to compare disease progression scores calculated for ultrasound images acquired at the same angle during different examinations.

<Effects>

As explained above, the ultrasound diagnostic apparatus 1100 relating to the present embodiment selects an ultrasound image signal of at least one frame from among ultrasound image signals of a plurality of frames acquired with respect to a subject through the ultrasound probe 1001, and displays the ultrasound image signal of the frame that is selected on the display 1008. The ultrasound diagnostic apparatus 1100 includes the control circuit 1010 which includes: the ultrasound image acquirer 2001 that acquires the ultrasound image signals of the plurality of frames; the evaluation target determiner 2002 that analyzes the ultrasound image signal of each of the frames and that determines the frame to be an evaluation target frame when the ultrasound image signal of the frame includes a target image section depicting a joint; the disease progression score calculator 2003 that calculates, for each evaluation target frame that is determined, a disease progression score quantifying activity of a disease, using an ultrasound image signal of the target image section included in the ultrasound image signal of the evaluation target frame; the selector 2004 that selects, in accordance with a predetermined numerical process, at least one disease progression score from among disease progression scores that are calculated; and the display controller 1006 that controls the display 1008 to display the disease progression score that is selected and an ultrasound image of a frame for which the disease progression score that is selected is calculated.

Through the configuration described above, disease activity can be evaluated using an ultrasound image selected, in accordance with the predetermined numerical process, from among a plurality of ultrasound images that are each acquired in a different direction.

Conventionally, due to an issue of which cross-section of a subject to evaluate through acquisition of an ultrasound image, a problem arises of evaluation results being dependent on procedural skill and subjective judgments of an examiner. In response to the aforementioned problem, the above configuration enables objective evaluation of disease activity through selection of an ultrasound image acquired using appropriate procedural technique. As a consequence, the above configuration reduces examiner dependency of an evaluation result of the disease evaluation.

<Other Modified Examples>

The above explains the ultrasound diagnostic apparatus relating to the embodiment. Note that the present invention is of course not limited to the embodiment, and various modifications may be made as appropriate based on the embodiment.

In the embodiment described above, the procedural technique judger 3004 judges that an ultrasound image signal of a frame has been acquired using appropriate procedural technique when a judgment result of step 1001 in FIG. 6 is "joint present", a judgment result of step S1002 is "motion noise not present", and a judgment result of step S1003 is "pressure not applied", and thus outputs a judgment result indicating "perform quantification" to the shape quantifier 2003A and the inflammation quantifier 2003B. In all other situations the procedural technique judger 3004 judges that the ultrasound image signal of the frame has not been acquired using appropriate procedural technique and outputs a judgment result of "suspend quantification, thereby completing processing with respect to the frame.

In an alternative configuration, the procedural technique judger 3004 may judge that an ultrasound image signal of a frame has been acquired using appropriate procedural technique when a judgment result of step S1001 is "joint present".

Further alternatively, the procedural technique judger 3004 may judge that an ultrasound image signal of a frame has been acquired using appropriate procedural technique when a judgment result of step S1001 is "joint present", and one out of (i) a judgment result of step S1002 is "motion noise not present", and (ii) a judgment result of step S1003 is "pressure not applied", is satisfied.

The above configuration enables the procedural technique judger 3004 to judge more simply whether or not an ultrasound image signal of a frame has been acquired using appropriate procedural skill, and thus enables faster selection of evaluation target frames to be used in disease progression score calculation.

In the embodiment described above, the disease progression scores are calculated according to the equations shown in MATH. 3 and 4, but the disease progression scores are not limited to being calculated according to aforementioned equations and may alternatively be any scores related to rheumatoid arthritis.

Furthermore, a method of evaluating a disease through selection of a disease progression score that quantifies disease activity is explained in the embodiment for an example in which the disease progression score relates to rheumatoid arthritis. However, the method described in the present disclosure is not limited to use with respect to rheumatoid arthritis and may alternatively be applied to any other disease for which disease activity can be quantified from an ultrasound image. For example, the method described in the present disclosure may be used to quantify disease activity of cancer by using an ultrasound image to quantify, for example, size of a tumor in an organ or a proportion of surface area of a tumor in which angiogenesis occurs.

In the above embodiment, the memory 1005 which is an example of a storage device is included in the ultrasound diagnostic apparatus 1100. However, the storage device is not limited to such a configuration and may alternatively be a semiconductor memory, a hard disk drive, an optical disk drive, a magnetic storage device, or the like that is connected to the ultrasound diagnostic apparatus 1100 from externally thereto.

Furthermore, although an example of configuration is explained in which the ultrasound probe 1001 and the display 1008 are connected to the ultrasound diagnostic apparatus 1100 from externally thereto, alternatively the aforementioned elements may all be integrated into the ultrasound diagnostic apparatus 1100.

The ultrasound probe 1001 may also include an inclination angle measurer such as an angle sensor and an inclination angle of the ultrasound probe 1001 which is measured may recorded in examination results in combination with corresponding disease progression scores.

In the embodiment described above, the ultrasound probe includes a plurality of piezoelectric elements that are arranged in a one dimensional array. However, the ultrasound probe is not limited to such a configuration. For example, alternatively the ultrasound probe may include a plurality of piezoelectric elements that are arranged in a two dimensional array. In a configuration in which the ultrasound probe includes piezoelectric elements arranged in a two dimensional array, irradiation position and direction of a transmitted ultrasound beam can be controlled by adjusting magnitude and timing of voltage application to each of the piezoelectric elements.

Note that the ultrasound probe may alternatively perform part of the function of the ultrasound transceiver. For example, the ultrasound probe may generate a transmission electrical signal based on a control signal output from the ultrasound transceiver for generation of the transmission electrical signal, and may convert the transmission electrical signal to ultrasound. The ultrasound probe may also convert reflected ultrasound received thereby to a reception electrical signal, and may generate a reception signal based on the reception electrical signal.

Typically process components included in the ultrasound diagnostic apparatus relating to the embodiment are implemented through a large scale integration (LSI) which is a type of integrated circuit (IC). Each of the components may be integrated individually into a single chip. Alternatively, some or all of the components may be collectively integrated into a single chip.

The embodiment was explained for an example in which each block is an independent piece of hardware. However, the blocks included in the ultrasound diagnostic apparatus are not limited to being independent pieces of hardware. For example, functions of each of the blocks may be implemented as necessary through a combination of a CPU and software.

With regards to functional blocks included in the ultrasound diagnostic apparatus, typically a portion or all of the functions of the functional blocks can be implemented through an LSI. Each of the functional blocks may be integrated individually into a single chip. Alternatively, some or all of the functional blocks may be collectively integrated into a single chip. Note that depending on the degree of integration, an LSI may be referred to as an IC, a system LSI, a super LSI, or an ultra LSI.

Furthermore, the method of circuit integration is not limited to an LSI and may alternatively be implemented through a dedicated circuit or a general processor. An FPGA which is programmable after the LSI is manufactured or a reconfigurable processor which allows for reconfiguration of the connection and setting of circuit cells inside the LSI may alternatively be used.

Furthermore, if technology for forming integrated circuits that replaces LSI were to emerge, owing to advances in semiconductor technology or to another derivative technology, the integration of functional blocks may naturally be accomplished using such technology.

Also, a portion or all of the functions of the ultrasound diagnostic apparatus relating to the embodiment may be implemented through execution of a program by a processor such as a CPU.

Furthermore, the present invention may alternatively be implemented as the aforementioned program or as a non-transitory computer recordable recording medium on which the program is recorded. Of course, the aforementioned program can also be distributed through a transfer medium such as the Internet.

Note that block diagrams referred to herein only illustrate one example of division of functional blocks. A plurality of the functional blocks may alternatively be implemented in combination as a single functional block, and likewise each one of the functional blocks may alternatively be divided and implemented as a plurality of separate functional blocks. Also, a portion of the functions of one of the functional blocks may be transferred to any other of the functional blocks. A single piece of hardware or software may be used to process functions of a plurality of functional blocks that have similar functions either in parallel or through a time division method.

Note that the order of steps described above is provided merely for explanation of one specific example of the present invention and such steps may alternatively be performed in a different order. Also, part of one of the aforementioned steps may be performed at the same time as (in parallel to) a different one of the aforementioned steps.

Functions of the ultrasound diagnostic apparatus relating to the embodiment and the modified examples thereof may be at least partially combined.

Of course the present invention also includes various modified examples of the embodiment which are within the scope of modifications that a person having ordinary skill in the art might consider.

<<Summary>>

As explained above, one aspect of the present disclosure relates to an ultrasound diagnostic apparatus for selecting an ultrasound image signal of at least one frame from among ultrasound image signals of a plurality of frames acquired with respect to a subject through an ultrasound probe, and displaying the ultrasound image signal of the frame that is selected on a display, the ultrasound diagnostic apparatus comprising a control circuit including: an ultrasound image acquirer that acquires the ultrasound image signals of the plurality of frames; an evaluation target determiner that analyzes the ultrasound image signal of each of the frames and that determines the frame to be an evaluation target frame when the ultrasound image signal of the frame includes a target image section depicting a joint; a disease progression score calculator that calculates, for each evaluation target frame that is determined, a disease progression score quantifying activity of a disease, the disease progression score calculator calculating the disease progression score using an ultrasound image signal of the target image section included in the ultrasound image signal of the evaluation target frame; a selector that selects, in accordance with a predetermined numerical process, at least one disease progression score from among disease progression scores that are calculated; and a display controller that controls the display to display the disease progression score that is selected and an ultrasound image of a frame for which the disease progression score that is selected is calculated.

Through the configuration described above, objectivity of evaluation is improved by evaluating disease activity using an ultrasound image of a cross-section selected, in accordance with the predetermined numerical process, from among a plurality of ultrasound images that are each acquired in a different direction. As a consequence, a degree to which an evaluation result of the disease evaluation is dependent on an examiner is reduced.

Alternatively, the evaluation target determiner may only determine the frame to be the evaluation target frame when detecting, from the ultrasound image signal of the frame, that the ultrasound probe does not apply pressure against a body surface of the subject during acquisition of the ultrasound image signal of the frame and that a Doppler signal appearing in the ultrasound image signal of the frame is not caused by motion noise.

The above configuration enables more accurate judgment for each frame of whether an ultrasound image signal of the frame is acquired using appropriate procedural technique and thus enables more accurate determination of evaluation target frames to be used in disease progression score calculation.

Alternatively, the predetermined numerical process may be a process of selecting, from among the disease progression scores that are calculated, a disease progression score that is identical or closest to at least one of a maximum disease progression score indicating a maximum disease activity, a mean disease progression score indicating an average disease activity, and a median disease progression score indicating an intermediate disease activity.

Through the above configuration, a selection criterion for selecting a most suitable disease progression score in accordance with the predetermined numerical process can be set as appropriate based on conditions such as state of a disease, characteristics of a subject, and examination guidelines of a doctor or hospital.

Alternatively, the ultrasound image signal may include a B-mode image signal and a Doppler mode image signal.

Alternatively, the disease may be rheumatoid arthritis.

Alternatively, the ultrasound diagnostic may further comprise: the ultrasound probe; and an angle detector that detects an inclination angle of the ultrasound probe, wherein the display controller may control the display to display the disease progression score and the inclination angle of the ultrasound probe during acquisition of the ultrasound image signal of the frame for which the disease progression score is calculated.

The above configuration enables simple comparison of disease progression scores calculated from ultrasound images acquired at the same inclination angle by recording an inclination angle for each disease progression score.

Alternatively, the ultrasound diagnostic apparatus may further comprise a storage device in which the ultrasound image signals of the plurality of frames are stored, wherein the selector may store the disease progression score selected thereby in the storage device.

The above configuration enables simple comparison with disease progression scores calculated from previously acquired ultrasound images when observing disease progression over time.

Alternatively, the ultrasound image signal of the target image section may be a B-mode image signal of an image section depicting an articular cavity, and the disease progression score calculator may calculate the disease progression score using an equation $GS = gsa \cdot GSx + gsb \cdot GSy + gsc \cdot GSz$, where GS represents the disease progression score, GSx represents a size of the image section depicting the articular cavity, GSy represents an average luminance of the image section depicting the articular cavity, GSz represents a degree of bone erosion, and gsa, gsb, and gsc are constants.

The above configuration improves objectivity of evaluation by calculating a disease progression score quantifying disease activity for each evaluation target frame using a signal of a target image section included in a B-mode image signal of the evaluation target frame.

Alternatively, the ultrasound image signal of the target image section may be a B-mode image signal and a Doppler mode image signal of an image section depicting an articular cavity, and the disease progression score calculator may calculate the disease progression score using an equation $PD = PDx/PDy$, where PD represents the disease progression score, PDy represents a surface area of a region of interest that is at least partially occupied by the image section depicting the articular cavity, and PDx represents a surface area occupied by pixels for which a Doppler signal is detected among pixels included in the region of interest.

The above configuration improves objectivity of evaluation by calculating a disease progression score quantifying disease activity for each evaluation target frame using a signal of a target image section included in a B-mode image signal and a Doppler mode image signal of the evaluation target frame.

Alternatively, the storage device may further store a previously calculated disease progression score and a selection criterion based on the predetermined numerical process, and the selector may determine the selection criterion by referring to the previously calculated disease progression score.

The above configuration enables disease progression score selection using the same selection criterion as used in selection of previously calculated disease progression scores. Therefore, the above configuration enables simple comparison with past evaluation results when observing disease progression over time, for example through periodic examinations.

Another aspect of the present disclosure relates to an ultrasound image processing method for selecting an ultrasound image signal of at least one frame from among ultrasound image signals of a plurality of frames acquired with respect to a subject through an ultrasound probe, and displaying the ultrasound image signal of the frame that is selected on a display, the ultrasound image processing method comprising: reading the ultrasound image signals of the plurality of frames from a storage device in which the ultrasound image signals are stored; analyzing the ultrasound image signal of each of the frames and determining the frame to be an evaluation target frame when the ultrasound image signal of the frame includes a target image section depicting a joint; calculating, for each evaluation target frame that is determined, a disease progression score quantifying activity of rheumatoid arthritis, the disease progression score being calculated using an ultrasound image signal of the target image section included in the ultrasound image signal of the evaluation target frame; selecting, in accordance with a predetermined numerical process, at least one disease progression score from among disease progression scores that are calculated; and controlling the display to display the disease progression score that is selected and an ultrasound image of a frame for which the disease progression score is calculated. Another aspect of the present disclosure relates to a non-transitory computer readable recording medium on which a program is recorded, wherein the program causes a computer to perform the aforementioned ultrasound image processing method.

The above configuration provides an ultrasound image processing method that reduces a degree to which an evaluation result of the disease evaluation is dependent on an examiner by selecting at least one ultrasound image acquired using appropriate procedural technique and objectively evaluating disease activity using the ultrasound image.

<<Supplementary Explanation>>

The embodiment described above is merely one preferable example of the present invention. Numbers, shapes, materials, configuration elements, location and connection of configuration elements, steps, orders of steps, and the like are merely examples and are not intended to in any way limit the present invention. Also note that among the configuration elements and steps described in the embodiment, configuration elements and steps that are not included in the independent claims, indicating a general concept of the present invention, are optional configuration elements and steps that are included in order to explain a preferable embodiment of the present invention.

In order to facilitate understanding, configuration elements are not necessarily illustrated to scale in the drawings referred to in the embodiment. The present invention is of course not limited by contents of the embodiment and various modifications may be made so long as such modifications do not deviate from the intended scope of the present invention.

In an ultrasound diagnostic apparatus, circuit components, leads, and the like are mounted on a substrate. Electrical wiring and circuits can be implemented in various different configurations based on common knowledge in the relevant technical field. However, as such configurations are not directly relevant to explanation of the present invention, explanation thereof is omitted. Also note that each of the diagrams is a schematic diagram and thus does not necessarily provide a strictly accurate illustration of the matter included therein.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic apparatus for selecting an ultrasound image signal of at least one frame from among ultrasound image signals of a plurality of frames acquired with respect to a subject through an ultrasound probe, and displaying the ultrasound image signal of the frame that is selected on a display, the ultrasound diagnostic apparatus comprising
a control circuit including:
an ultrasound image acquirer that acquires the ultrasound image signals of the plurality of frames;
an evaluation target determiner that analyzes the ultrasound image signal of each of the frames and that determines the frame to be an evaluation target frame when the frame fulfills both a first condition (i) and a second condition (ii), the first condition (i) being that the ultrasound image signal of the frame includes a target image section depicting a joint, and the second condition (ii) being that an evaluation value for the frame based on the ultrasound image signal of the frame satisfies a predetermined condition, which indicates that the frame has been acquired at least one of with the probe not applying pressure against a body surface of the subject or with motion noise not present;
a disease progression score calculator that calculates, for each evaluation target frame that is determined, a disease progression score quantifying activity of a disease, the disease progression score calculator calculating the disease progression score using an ultrasound image signal of the target image section included in the ultrasound image signal of the evaluation target frame;
a selector that selects, in accordance with a predetermined numerical process, at least one disease progression score from among disease progression scores that are calculated; and
a display controller that controls the display to display the disease progression score that is selected and an ultrasound image of a frame for which the disease progression score that is selected is calculated, and
wherein each of the ultrasound image acquirer, the evaluation target determiner, the disease progression score calculator, the selector, and the display controller comprises a hardware circuit or a programmable device that is a part of the control circuit.

2. The ultrasound diagnostic apparatus of claim 1, wherein
the evaluation target determiner determines the frame fulfills the second condition (ii) by at least one of a pressure detector that receives the ultrasound image signal of a frame and judges whether the ultrasound probe does not apply pressure against a body surface of the subject during acquisition of the ultrasound image signal of the frame, or a motion noise detector that receives the ultrasound image signal of the frame and judges whether a Doppler signal appearing in the ultrasound image signal of the frame is not caused by motion noise.

3. The ultrasound diagnostic apparatus of claim 1, wherein
the predetermined numerical process is a process of selecting, from among the disease progression scores that are calculated, a disease progression score that is identical or closest to at least one of a maximum disease progression score indicating a maxi um disease activity, a mean disease progression score indicating an average disease activity, and a median disease progression score indicating an intermediate disease activity.

4. The ultrasound diagnostic apparatus of claim 1, wherein
the ultrasound image signal includes a B-mode image signal and a Doppler mode image signal.

5. The ultrasound diagnostic apparatus of claim 4, wherein
the ultrasound image signal of the target image section is a B-mode image signal of an image section depicting an articular cavity, and
the disease progression score calculator calculates the disease progression score using an equation $$GS = gsa \cdot GSx + gsb \cdot GSy + gsc \cdot GSz$$

where GS represents the disease progression score, GSx represents a size of the image section depicting the articular cavity, GSy represents an average luminance of the image section depicting the articular cavity, GSz represents a degree of bone erosion, and gsa, gsb, and gsc are constants.

6. The ultrasound diagnostic apparatus of claim 4, wherein
the ultrasound image signal of the target image section is a B-mode image signal and a Doppler mode image signal of an image section depicting an articular cavity, and
the disease progression score calculator calculates the disease progression score using an equation $$PD = PDx/PDy$$

where PD represents the disease progression score, PDy represents a surface area of a region of interest that is at least partially occupied by the image section depicting the articular cavity, and PDx represents a surface area occupied by pixels for which a Doppler signal is detected among pixels included in the region of interest.

7. The ultrasound diagnostic apparatus of claim 6, wherein
PDy is a fixed value.

8. The ultrasound diagnostic apparatus of claim 1, wherein
the disease is rheumatoid arthritis.

9. The ultrasound diagnostic apparatus of claim 1, further comprising:
the ultrasound probe; and
an angle detector that detects an inclination angle of the ultrasound probe, wherein
the angle detector is a hardware circuit or a programmable device that is a part of the control circuit, and
the display controller controls the display to display the disease progression score and the inclination angle of the ultrasound probe during acquisition of the ultrasound image signal of the frame for which the disease progression score is calculated.

10. The ultrasound diagnostic apparatus of claim 1, further comprising
a storage device in which the ultrasound image signals of the plurality of frames are stored, wherein
the selector stores the disease progression score selected thereby in the storage device.

11. The ultrasound diagnostic apparatus of claim 10, wherein
the storage device further stores a previously calculated disease progression score and a selection criterion based on the predetermined numerical process, and
the selector determines the selection criterion by referring to the previously calculated disease progression score.

12. An ultrasound image processing method for selecting an ultrasound image signal of at least one frame from among ultrasound image signals of a plurality of frames acquired with respect to a subject through an ultrasound probe, and displaying the ultrasound image signal of the frame that is selected on a display, the ultrasound image processing method comprising:
reading the ultrasound image signals of the plurality of frames from a storage device in which the ultrasound image signals are stored;
analyzing the ultrasound image signal of each of the frames and determining the frame to be an evaluation target frame when the frame fulfills both a first condition (i) and a second condition (ii), the first condition (i) being that the ultrasound image signal of the frame includes a target image section depicting a joint, and the second condition (ii) being that an evaluation value for the frame based on the ultrasound image signal of the frame satisfies a predetermined condition, which indicates that the frame has been acquired at least one of with the probe not applying pressure against a body surface of the subject or with motion noise not present;
calculating, for each evaluation target frame that is determined, a disease progression score quantifying activity of rheumatoid arthritis, the disease progression score being calculated using an ultrasound image signal of the target image section included in the ultrasound image signal of the evaluation target frame;
selecting, in accordance with a predetermined numerical process, at least one disease progression score from among disease progression scores that are calculated; and controlling the display to display the disease progression score that is selected and an ultrasound image of a frame for which the disease progression score is calculated.

13. The ultrasound image processing method of claim 12, wherein
in the determining, the frame is only determined to fulfill the second condition (ii) when detecting, from the ultrasound image signal of the frame, at least one of that the ultrasound probe does not apply pressure against a body surface of the subject during acquisition of the ultrasound image signal of the frame by a pressure detector, or that a Doppler signal appearing in the ultrasound image signal of the frame is not caused by motion noise by a motion noise detector.

14. The ultrasound image processing method of claim 12, wherein
the predetermined numerical process is a process of selecting, from among the disease progression scores that are calculated, a disease progression score that is identical or closest to at least one of a maximum disease progression score indicating a maximum disease activity, a mean disease progression score indicating an average disease activity, and a median disease progression score indicating an intermediate disease activity.

15. The ultrasound image processing method of claim 12, wherein
the ultrasound image signal includes a B-mode image signal and a Doppler mode image signal.

16. The ultrasound image processing method of claim 15, wherein
the ultrasound image signal of the target image section is a B-mode image signal of an image section depicting an articular cavity, and
in the calculating, the disease progression score is calculated using an equation $GS = gsa \cdot GSx + gsb \cdot GSy + gsc \cdot GSz$ where GS represents the disease progression score, GSx represents a size of the image section depicting the articular cavity, GSy represents an average luminance of the image section depicting the articular cavity, GSz represents a degree of bone erosion, and gsa, gsb, and gsc are constants.

17. The ultrasound image processing method of claim 15, wherein
the ultrasound image signal of the target image section is a B-mode image signal and a Doppler mode image signal of an image section depicting an articular cavity, and
in the calculating, the disease progression score is calculated using an equation $PD = PDx/PDy$ where PD represents the disease progression score, PDy represents a surface area of a region of interest that is at least partially occupied by the image section depicting the articular cavity, and PDx represents a surface area occupied by pixels for which a Doppler signal is detected among pixels included in the region of interest.

18. A non-transitory computer readable recording medium on which a program is recorded, wherein
the program causes a computer to perform the ultrasound image processing method of claim 12.

* * * * *